US008357516B2

(12) United States Patent
Hirai et al.

(10) Patent No.: US 8,357,516 B2
(45) Date of Patent: Jan. 22, 2013

(54) PRIMER SET FOR AMPLIFICATION OF UGT1A1 GENE, REAGENT FOR AMPLIFICATION OF UGT1A1 GENE CONTAINING THE SAME, AND THE USES THEREOF

(75) Inventors: Mitsuharu Hirai, Kyoto (JP); Satoshi Majima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 273 days.

(21) Appl. No.: 12/293,954

(22) PCT Filed: Nov. 29, 2007

(86) PCT No.: PCT/JP2007/073107
§ 371 (c)(1),
(2), (4) Date: Sep. 22, 2008

(87) PCT Pub. No.: WO2008/066136
PCT Pub. Date: Jun. 5, 2008

(65) Prior Publication Data
US 2009/0208954 A1    Aug. 20, 2009

(30) Foreign Application Priority Data

Nov. 30, 2006 (JP) ................................. 2006-322955
Sep. 7, 2007 (JP) ................................. 2007-232611

(51) Int. Cl.
*C12P 19/34* (2006.01)
(52) U.S. Cl. ...................................................... 435/91.2
(58) Field of Classification Search .................. 435/91.2
See application file for complete search history.

(56) References Cited

U.S. PATENT DOCUMENTS

| | | | |
|---|---|---|---|
| 4,889,818 A | 12/1989 | Gelfand et al. | |
| 5,079,352 A | 1/1992 | Gelfand et al. | |
| 6,395,481 B1 | 5/2002 | Di Rienzo et al. | |
| 6,479,236 B2 * | 11/2002 | Penny et al. | 435/6 |
| 7,625,699 B2 * | 12/2009 | Devlin et al. | 435/6 |
| 2006/0160074 A1 | 7/2006 | Dorn et al. | |
| 2006/0257960 A1 | 11/2006 | Sato et al. | |
| 2006/0281098 A1 | 12/2006 | Miao et al. | |
| 2008/0153093 A1 | 6/2008 | Okamura et al. | |

FOREIGN PATENT DOCUMENTS

| | | |
|---|---|---|
| EP | 0 455 430 A2 | 11/1991 |
| EP | 1 352 970 | 10/2003 |
| EP | 1 352 970 A1 | 10/2003 |
| GB | 2432365 A | 5/2007 |
| JP | 2004-73035 A | 3/2004 |
| JP | 2005-58107 A | 3/2005 |
| JP | 2005-261354 A | 9/2005 |
| JP | 2006-526412 A | 11/2006 |
| WO | WO 91/09950 A1 | 7/1991 |
| WO | WO 92/09689 A1 | 6/1992 |
| WO | 99/57322 | 11/1999 |
| WO | 01/79230 | 10/2001 |
| WO | WO 02/48400 A1 | 6/2002 |
| WO | WO 03/013537 A2 | 2/2003 |
| WO | WO 2004/108954 A1 | 12/2004 |
| WO | WO 2005087952 * | 9/2005 |
| WO | 2006/027182 A1 | 3/2006 |

OTHER PUBLICATIONS

Buck et al., Biotechniques, vol. 27, No. 3, pp. 528-536, 1999.*
Lowe et al., Nucleic Acids Research, vol. 18, No. 7, pp. 1757-1761, 1990.*
International Search Report of PCT/JP2007/073107, dated Jan. 8, 2008.
Ando et al. "Polymorphisms of UDP-Glucuronosyltransferase Gene and Irinotecan Toxicity: A Pharmacogenetic Analysis." Cancer Research, 60, Dec. 15, 2000, pp. 6921-6926.
Tanabe et al. "The 26th Annual Meeting of Japanese Society of Clinical Pharmacology and Therapeutics," Partial Japanese Journal of Clinical Pharmacology and Therapeutics, vol. 36, 2005, pp. S187.
Supplementary European Search Report issued in corresponding European Application No. 07 83 2807.7 and mailed Nov. 5, 2009.
Database EMBL [Online], Nov. 9, 2005, "Method for detection of mutation in UGT Gene", XP002549501 retrieved from EBI accession No. EMBL: BD438297, Database accession No. BD438297.
Araki et al., "Pharmacogenetic impact of polymorphisms in the coding region of the UGT1A1 gene on SN-38 glucuronidation in Japanese patients with cancer," Cancer Science, 97: 1255-1259 (2006).
Hasegawa et al., "Rapid Detection of UGT1A1 Gene Polymorphisms by Newly Developed Invader Assay," Clinical Chemistry, 50: 1479-1480 (2004).
Hiratsuka et al., "Genetic testng for pharmacogentics and its clinical application in drug therapy," Clinica Chimica Acta, 363:177-186 (2006).
Monaghan et al., "Genetic variation in bilirubin UDP-glucuronosyltransferase gene promoter and Gilbert's syndrome," The Lancet, 347: 578-581 (1996).
Extended Search Report issued in corresponding European Patent Application No. 12158063.3 dated May 2, 2012.
Office Action issued in corresponding European Patent Application No. 07832807.7 dated May 15, 2012.
Office Action issued in corresponding Chinese Patent Application No. 201110046882.1 dated Apr. 6, 2011.
Office Action issued in corresponding Chinese Patent Application No. 201110046899.7 dated Apr. 6, 2012.

* cited by examiner

*Primary Examiner* — Gary Benzion
*Assistant Examiner* — Cynthia Wilder
(74) *Attorney, Agent, or Firm* — Morgan, Lewis & Bockius LLP

(57) ABSTRACT

Primer sets for amplifying target regions containing sites to be detected in the UGT1A1 gene by a gene amplification method are provided, wherein the primer sets can amplify the regions specifically. Three pairs of primer sets are used including forward primers consisting of the base sequences of SEQ ID NOs: 4 or 81, 21, and 42 as well as reverse primers consisting of the base sequences of SEQ ID NOs: 13 or 91, 29 and 48, respectively. The use of these primer sets makes it possible to amplify three target regions including parts where three types of polymorphisms (UGT1A1*6, UGT1A1*27, and UGT1A1*28) of the UGT1A1 gene are generated, respectively, in the same reaction solution at the same time.

12 Claims, 4 Drawing Sheets

PRIMER SET FOR AMPLIFICATION OF UGT1A1 GENE, REAGENT FOR AMPLIFICATION OF UGT1A1 GENE CONTAINING THE SAME, AND THE USES THEREOF

TECHNICAL FIELD

The present invention relates to primer sets for amplifying the UGT1A1 gene, reagents for amplifying the UGT1A1 gene containing the same, and the uses thereof.

BACKGROUND ART

UDP-Glucuronosyl Transferase (UGT) is an enzyme that catalyzes the reaction of adding glucuronic acid to, for example, a drug, a foreign substance, or an endogenous substance such as bilirubin, steroid hormone, or bile acid. It is known as a drug-metabolizing enzyme. A plurality of isozymes that are classified into the UGT1 family and the UGT2 family have been reported as the UGT. Genetic polymorphisms exist in a gene (UGT1A1 gene) that codes UGT1A1 belonging to the UGT1 family among those isozymes. Generally, they are said to be involved in the incidence of side effects of irinotecan hydrochloride, an anticancer agent. Specifically, it has been reported that when a patient has a UGT1A1 gene polymorphism, the function of detoxifying irinotecan hydrolysate (SN-38) having high antitumor activity by using the UGT is deteriorated, which causes serious side effects such as a decrease in the number of white blood cells and diarrhea. Known examples of typical genetic polymorphisms involved in such side effects include UGT1A1*28, a polymorphism in a promoter region, as well as UGT1A1*6 and UGT1A1*27, polymorphisms in exon 1. Particularly, it has been reported that in addition to UGT1A1*28, the most important polymorphism, Asians including Japanese also have at least one of polymorphisms, UGT1A1*6 and UGT1A1*27, in combination therewith and thereby stronger side effects tend to be manifested. Furthermore, since UGT1A1 is involved in bilirubin conjugation formed through glucuronic acid in vivo, the polymorphisms thereof also cause constitutional jaundice such as Gilbert syndrome. Accordingly, the examination of a plurality of polymorphisms with respect to the UGT1A1 gene is very important to predict the degree and the onset of side effect to be caused by an anticancer agent.

On the other hand, the detection of a point mutation, a so-called single nucleotide polymorphism (SNP), is employed widely as a method of analyzing, at the gene level, for example, the causes of all types of diseases and the individual differences in disease liability (susceptibility to diseases) and in drug action. Examples of the common methods of detecting a point mutation include: (1) a direct sequencing method in which the region corresponding to a sequence to be detected in a target DNA of a sample is amplified by a polymerase chain reaction (PCR) and all the gene sequences are analyzed, (2) a RFLP analysis in which the region corresponding to a sequence to be detected in a target DNA of a sample is amplified by PCR, the amplification product thus obtained is cut with a restriction enzyme whose cleaving action differs depending on the presence or absence of the target mutation in the sequence to be detected and is then electrophoresed, and thereby typing is performed, and (3) the ASP-PCR method in which PCR is performed using a primer with a target mutation located at the 3'-end region and the mutation is judged depending on the presence or absence of amplification.

However, since these methods require, for example, purification of DNA extracted from a sample, electrophoresis, and a treatment with a restriction enzyme, they take time and cost. Furthermore, after PCR is performed, it is necessary to open the reaction container once. Accordingly, there is a possibility that the amplification product may contaminate the next reaction system and thereby the analysis accuracy may be deteriorated. Moreover, since it is difficult to automate, a large amount of samples cannot be analyzed. Further, the aforementioned ASP-PCR method (3) is less specific, which also is a problem.

Because of these problems, recently, a method of analyzing the melting temperature (Tm) of double-stranded nucleic acid formed of a probe and target nucleic acid is used as a method of detecting a point mutation. Since such a method is performed through, for example, Tm analysis or analysis of the melting curve of the double strand, it is referred to as melting curve analysis. This method is described below. That is, first, a probe complementary to a sequence to be detected containing a target point mutation is used to form a hybrid (double-stranded DNA) between the aforementioned probe and a target single-stranded DNA contained in a detection sample. Subsequently, this hybridization product is heat-treated, and dissociation (melting) of the hybrid accompanying the temperature rise is detected by a change in a signal such as absorbance. The Tm value then is determined based on the result of the detection and the presence or absence of any point mutation is judged accordingly. The higher the homology of the hybridization product, the higher the Tm value, and the lower the homology, the lower the Tm value. Therefore the Tm value (reference value for assessment) is determined beforehand with respect to the hybridization product between the sequence to be detected containing a point mutation and a probe complementary thereto, and then the Tm value (measured value) of the hybridization product between the target single-stranded DNA contained in the detection sample and the aforementioned probe is measured. When the measured value is comparable to the reference value, it is considered as matching, that is, it can be judged that a point mutation is present in the target DNA. On the other hand, when the measured value is lower than the reference value, it is considered as mismatching, that is, it can be judged that no point mutation is present in the target DNA. Furthermore, according to this method, it also is possible to automate gene analysis.

However, such a detection method using Tm analysis also has a problem in that a region including a site to be detected must be able to be amplified specifically and efficiently in PCR. Particularly, many isozymes are present in UGT and the sequences for coding them also are very similar to one another. Accordingly, there is a possibility that genes coding isozymes other than UGT1A1 also are amplified in PCR. Furthermore, when other isozyme-coding genes also have been amplified as described above, it may cause a decrease in the reliability of the analysis result in the analysis of a particular polymorphism (UGT1A1*28, UGT1A1*6, or UGT1A1*27) of the UGT1A1 gene (Nonpatent Document 1). Moreover, as described above, since the analysis of one sample is accompanied by a considerable amount of time and energy, it is not practical to analyze a large amount of samples, which also is a problem.

[Nonpatent Document 1] PMID: 11156391 Cancer Res. 2000 Dec. 15; 60(24): 6921-6.

DISCLOSURE OF INVENTION

Hence, the present invention is intended to provide primer sets for specifically amplifying a target region in the UGT1A1 gene by a gene amplification method.

In order to achieve the aforementioned object, a primer set of the present invention is a primer set for amplifying the UGT1A1 gene by a gene amplification method, wherein the primer set includes at least one selected from the group consisting of the following primer sets (1) to (3):

Primer Set (1):

a primer set of a pair of primers including a forward primer composed of the following oligonucleotide (F1) and a reverse primer composed of the following oligonucleotide (R1):

(F1): at least one oligonucleotide selected from:

oligonucleotide that is at least one oligonucleotide having a sequence identical to that of a region extending from adenine (A) at base 2120 to be considered as the first base to any one of the $18^{th}$ to $22^{nd}$ bases in the direction toward the 5' end in the UGT1A1 gene consisting of the base sequence of SEQ ID NO: 1, with the adenine (A) being the 3' end, and oligonucleotide that is at least one oligonucleotide having a sequence identical to that of a region extending from cytosine (C) at base 2140 to be considered as the first base to any one of the $18^{th}$ to $34^{th}$ bases in the direction toward the 5' end in the UGT1A1 gene consisting of the base sequence of SEQ ID NO: 1, with the cytosine (C) being the 3' end, (R1): at least one oligonucleotide selected from:

oligonucleotide that is at least one oligonucleotide complementary to a region extending from guanine (G) at base 2226 to be considered as the first base to any one of the $17^{th}$ to $27^{th}$ bases in the direction toward the 3' end in the UGT1A1 gene consisting of the base sequence of SEQ ID NO: 1, with cytosine (C) complementary to the guanine (G) at base 2226 being the 3' end, and oligonucleotide that is at least one oligonucleotide complementary to a region extending from cytosine (C) at base 2198 to be considered as the first base to any one of the $22^{nd}$ to $39^{th}$ bases in the direction toward the 3' end in the UGT1A1 gene consisting of the base sequence of SEQ ID NO: 1, with guanine (G) complementary to the cytosine (C) at base 2198 being the 3' end, Primer set (2):

a primer set of a pair of primers including a forward primer composed of the following oligonucleotide (F2) and a reverse primer composed of the following oligonucleotide (R2):

(F2): oligonucleotide that is at least one oligonucleotide having a sequence identical to that of a region extending from guanine (G) at base 2622 to be considered as the first base to any one of the $15^{th}$ to $27^{th}$ bases in the direction toward the 5' end in the UGT1A1 gene consisting of the base sequence of SEQ ID NO: 1, with the guanine (G) being the 3' end, and (R2): oligonucleotide that is at least one oligonucleotide complementary to a region extending from cytosine (C) at base 2687 to be considered as the first base to any one of the $17^{th}$ to $26^{th}$ bases in the direction toward the 3' end in the UGT1A1 gene consisting of the base sequence of SEQ ID NO: 1, with guanine (G) complementary to the cytosine (C) at base 2687 being the 3' end, and Primer Set (3):

a primer set of a pair of primers including a forward primer composed of the following oligonucleotide (F3) and a reverse primer composed of the following oligonucleotide (R3):

(F3): oligonucleotide that is at least one oligonucleotide having a sequence identical to that of a region extending from cytosine (C) at base 1863 to be considered as the first base to any one of the $17^{th}$ to $31^{st}$ bases in the direction toward the 5' end in the UGT1A1 gene consisting of the base sequence of SEQ ID NO: 1, with the cytosine (C) being the 3' end, and (R3): oligonucleotide that is at least one oligonucleotide complementary to a region extending from cytosine (C) at base 1928 to be considered as the first base to any one of the $16^{th}$ to $20^{th}$ bases in the direction toward the 3' end in the UGT1A1 gene consisting of the base sequence of SEQ ID NO: 1, with guanine (G) complementary to the cytosine (C) at base 1928 being the 3' end.

A reagent for amplifying a gene of the present invention is a reagent for amplifying the UGT1A1 gene by a gene amplification method, wherein the reagent includes the primer set for amplifying the UGT1A1 gene of the present invention.

A method of manufacturing an amplification product of the present invention is a method of manufacturing an amplification product of the UGT1A1 gene by a gene amplification method, wherein the method includes the following step (I):

(I) amplifying the UGT1A1 gene in a reaction solution using a primer set for amplifying the UGT1A1 gene according to the present invention, with nucleic acid contained in a sample being used as a template.

A polymorphism analysis method of the present invention is a method of analyzing a polymorphism of a site to be detected in the UGT1A1 gene, wherein the method includes the following steps (i) to (iv):

(i) amplifying a region including a site to be detected in the UGT1A1 gene in a reaction solution by a method of manufacturing an amplification product of the present invention, (ii) preparing a reaction solution that contains the amplification product obtained in step (i) and a probe capable of hybridizing to the site to be detected, (iii) measuring signal values that indicate melting states of a hybridization product between the amplification product and the probe while changing the temperature of the reaction solution, and (iv) determining a polymorphism of the site to be detected from a change in the signal values accompanying a change in the temperature.

The primer set of the present invention makes it possible specifically and efficiently to amplify a target region in a reaction solution, with the target region including the site where a polymorphism to be detected (UGT1A1*28, UGT1A1*6, or UGT1A1*27) is generated in the UGT1A1 gene. Accordingly, the time and cost can be reduced, which is different from the conventional methods described above. Furthermore, as described above, since a region including a site to be detected where a specific polymorphism of the UGT1A1 gene is generated can be amplified specifically, for example, further the use of a probe complementary to a sequence to be detected including the site to be detected makes it possible to perform Tm analysis by directly using the aforementioned reaction solution to type the polymorphism. Moreover, since amplification of the target region and typing of the polymorphism can be performed with one reaction solution, it is also possible to automate the operation. Since the use of the primer set of the present invention allows a pretreatment to be omitted even in the case of, for example, a contaminated sample (for instance, whole blood or oral mucosa), the amplification reaction can be carried out quicker and more simply. Furthermore, since the use of the primer set of the present invention allows the amplification reaction to be carried out with higher amplification efficiency as compared to the conventional case, the amplification reaction time also can be shortened. Thus, according to the primer set of the present invention and a reagent including the same as well as the method of manufacturing an amplification product and a polymorphism analysis method, in each of which the primer set and the reagent are used, polymorphisms in the UGT1A1 gene can be analyzed quickly and simply, and it therefore can be said that they are very effective in the field of medicine.

BEST MODE FOR CARRYING OUT THE INVENTION

<Primer Set for Amplifying UGT1A1 Gene>

Figure 1:
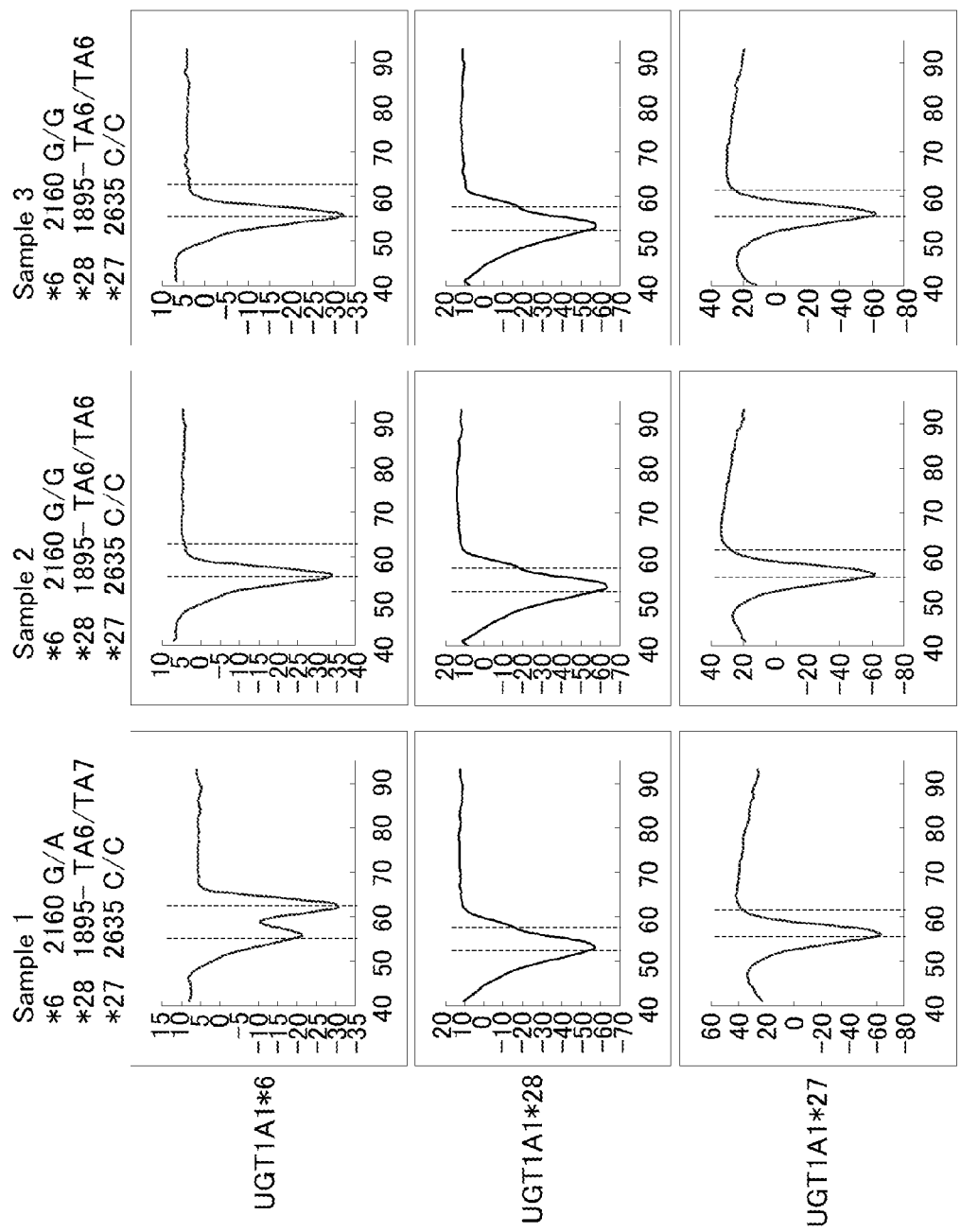
FIG. 1 shows graphs indicating the results of Tm analysis in Example 1 of the present invention.

As described above, the primer set for amplifying the UGT1A1 gene of the present invention is characterized by including at least one primer set selected from the group consisting of the aforementioned primer sets (1) to (3). The inclusion of at least one of the primer sets makes it possible, for example, to amplify specifically a specific target region in the UGT1A1 gene.

The primer set for amplifying the UGT1A1 gene of the present invention may include, for example, one of the aforementioned primer sets (1) to (3) or may include two or all of the primer sets (1) to (3). As described later, the target region that can be amplified specifically with the primer set (1) is a region including a site where the polymorphism UGT1A1*6 is generated in the UGT1A1 gene; the target region that can be amplified specifically with the primer set (2) is a region including a site where the polymorphism UGT1A1*27 is generated in the UGT1A1 gene; and the target region that can be amplified specifically with the primer set (3) is a region including a site where the polymorphism UGT1A1*28 is generated in the UGT1A1 gene.

As described above, since these three types of polymorphisms in the UGT1A1 gene are known as polymorphisms that affect drug metabolism, it is considered to be important to examine not only one of them but two or all of the three types of polymorphisms. However, the conventional methods have a problem in that a plurality of sequences cannot be analyzed in one reaction system. Conceivably, as described above, this is because the many isozymes exist in a UGT and thereby genes coding isozymes other than UGT1A1 also are amplified in PCR. Accordingly, in order to examine two or all of the three types of polymorphisms (UGT1A1*28, UGT1A1*6, and UGT1A1*27) in the UGT1A1 gene, it is necessary that the regions including the sites where the respective polymorphisms are generated are amplified in separate reaction systems, respectively, and the resultant amplification products are analyzed separately. Thus, with the conventional methods, it is very difficult to use only the UGT1A1 gene selected from the UGT genes as a template and to amplify specifically only two or three types of target regions including the sites where polymorphisms are generated, respectively, in the UGT1A1 gene. Furthermore, since such analysis of even one sample is accompanied by a considerable amount of work, there is a problem in that the analysis of a large amount of samples is not practical. On the contrary, according to the primer set for amplifying the UGT1A1 gene of the present invention, even in the case where two or all of the three types of the primer sets (1) to (3) are included, the respective target regions can be amplified in the same reaction solution simultaneously and specifically. Accordingly, the time and cost can be reduced, which is different from the aforementioned conventional methods. Furthermore, since two or three target regions are amplified specifically in the same reaction solution as described above, for example, the use of a probe complementary to a sequence to be detected in each target region makes it possible to perform Tm analysis directly using the aforementioned reaction solution to type each of the two or three types of polymorphisms. As described above, since two or three types of polymorphisms in the UGT1A1 gene can be analyzed in the same reaction solution, it is suitable for the primer set for amplifying the UGT1A1 gene of the present invention not only to include one of the primer sets (1) to (3) but also to include two or three of them. When not only one target region but also two or three target regions are amplified simultaneously using such a UGT1A1 gene primer set, polymorphisms in the UGT1A1 gene can be analyzed more efficiently as compared to the conventional cases.

Hereinafter, a forward primer also may be referred to as "F primer" and a reverse primer as "R primer".

As described above, the primer set (1) is a primer set of a pair of primers including a forward primer composed of the following oligonucleotide (F1) and a reverse primer composed of the following oligonucleotide (R1):

(F1): at least one oligonucleotide selected from:

oligonucleotide that is at least one oligonucleotide having a sequence identical to that of a region extending from adenine (A) at base 2120 to be considered as the first base to any one of the $18^{th}$ to $22^{nd}$ bases in the direction toward the 5' end in the UGT1A1 gene consisting of the base sequence of SEQ ID NO: 1, with the adenine (A) being the 3' end, and oligonucleotide that is at least one oligonucleotide having a sequence identical to that of a region extending from cytosine (C) at base 2140 to be considered as the first base to any one of the $18^{th}$ to $34^{th}$ bases in the direction toward the 5' end in the UGT1A1 gene consisting of the base sequence of SEQ ID NO: 1, with the cytosine (C) being the 3' end, (R1): at least one oligonucleotide selected from:

oligonucleotide that is at least one oligonucleotide complementary to a region extending from guanine (G) at base 2226 to be considered as the first base to any one of the $17^{th}$ to $27^{th}$ bases in the direction toward the 3' end in the UGT1A1 gene consisting of the base sequence of SEQ ID NO: 1, with cytosine (C) complementary to the guanine (G) at base 2226 being the 3' end, and oligonucleotide that is at least one oligonucleotide complementary to a region extending from cytosine (G) at base 2198 to be considered as the first base to any one of the $22^{nd}$ to $39^{th}$ bases in the direction toward the 3' end in the UGT1A1 gene consisting of the base sequence of SEQ ID NO: 1, with guanine (G) complementary to the cytosine (C) at base 2198 being the 3' end.

The base sequence indicated in SEQ ID NO: 1 is a full-length sequence of the UGT1A1 gene of human (*Homo sapiens*)-derived UGT1 family and, for example, has been registered at NCBI under the accession No AY603772.

The primer set (1) is a primer set for amplifying a DNA strand including any one of a region from base 2121 to base 2225, a region from base 2141 to base 2197, a region from base 2121 to 2197, and a region from base 2141 to 2225 in SEQ ID NO: 1, as well as a strand complementary thereto. Base 2160 in this region (i.e. base 2160 in SEQ ID NO: 1) is known for the presence of a point mutation (2160G, 2160A) that affects the function of UGT1A1, and the polymorphism thereof is UGT1A1*6 described above. In the present invention, the polymorphism of this site can be indicated as 2060G/G or 2160A/A in the case of homozygote and as 2160G/A in the case of heterozygote. Hereinafter, this primer set (1) also may be referred to as a "primer set for UGT1A1*6". When only the polymorphism UGT1A1*6 is to be analyzed, it is sufficient to use only the primer set for UGT1A1*6.

In the present invention, the F1 primer and R1 primer of the primer set (1) can be any primers, as long as the base located at the 3' end that serves to determine the site from which DNA polymerase starts amplification satisfies the aforementioned condition. Fixation of the base located at the 3' end of each primer in this manner makes it possible to sufficiently prevent the primer set (1) from being bound to, for example, another similar isozyme gene (for example, UGT1A3 gene or UGT1A4 gene).

As described above, since the F1 primer and R1 primer each can be any primer as long as the base located at the 3' end is fixed, the length itself of each primer is not particularly limited and can be adjusted suitably to be common length. The length of the primers is, for example, in the range of 13- to 50-mers, preferably 14- to 45-mers, and more preferably 15- to 40-mers. Specifically, it is preferable that the F1 primer be: at least one oligonucleotide having a sequence identical to that of a region extending from adenine (A) at base 2120 to be considered as the first base to any one of the $18^{th}$ to $22^{nd}$ bases (preferably the $19^{th}$ to $22^{nd}$ bases and more preferably the $19^{th}$ to $21^{st}$ bases) in the direction toward the 5' end in the base sequence of SEQ ID NO: 1; or at least one oligonucleotide having a sequence identical to that of a region extending from cytosine (C) at base 2140 to be considered as the first base to any one of the $18^{th}$ to $34^{th}$ bases (preferably the $21^{st}$ to $33^{rd}$ bases and more preferably the $24^{th}$ to $31^{st}$ bases) in the direction toward the 5' end in the base sequence of SEQ ID NO: 1. Furthermore, it is preferable that the R1 primer be: at least one oligonucleotide complementary to a region extending from guanine (G) at base 2226 to be considered as the first base to any one of the $17^{th}$ to $27^{th}$ bases (preferably the $19^{th}$ to $26^{th}$ bases and more preferably the $19^{th}$ to $23^{rd}$ bases) in the direction toward the 3' end in the base sequence of SEQ ID NO: 1; or at least one oligonucleotide complementary to a region extending from cytosine (C) at base 2198 to be considered as the first base to any one of the $22^{nd}$ to $39^{th}$ bases (preferably the $23^{rd}$ to $36^{th}$ bases and more preferably the $25^{th}$ to $34^{th}$ bases) in the direction toward the 3' end in the base sequence of SEQ ID NO: 1. Since each 3' end of the F1 primer and the R1 primer is fixed, the region to be elongated from the primer is, for example, one of a region from base 2121 to base 2225, a region from base 2141 to base 2197, a region from base 2121 to base 2197, and a region from base 2141 to base 2225 in SEQ ID NO: 1 as described above. However, the length of the whole amplification product obtained varies according to the length of the primer to be used.

Furthermore it is not necessary for the R1 primer and the F1 primer to be oligonucleotides perfectly complementary to the base sequence indicated in SEQ ID NO: 1 and to the strand complementary to the base sequences respectively. In other words, the part excluding the base located at the 3' end in each primer may be different in one to five bases from that of a perfectly complementary oligonucleotide.

Specific examples of the F1 primer and the R1 primer are indicated below but the present invention is not limited thereto. The combination of these F1 primer and R1 primer is not limited by any means. Specifically, however, a primer set (1') is particularly preferable, which includes a F1' primer composed of oligonucleotide of SEQ ID NO: 4 or SEQ ID NO 81, and a R1' primer composed of oligonucleotide of SEQ ID NO: 13 or SEQ ID NO: 91. "Tm (° C.)" indicated below in the table is Tm (° C.) obtained when each sequence indicated below in the table was hybridized with the sequence perfectly complementary thereto. The "Tm (° C.)" is a value calculated by using MELTCALC software (meltcalc.com/), with parameters including an oligonucleotide concentration of 0.2 μM and a sodium equivalent (Na eq.) of 50 mM (the same applies below). The Tm value can be calculated by using, for example, conventionally known MELTCALC software (meltcalc.com/) or also can be determined by the nearest neighbor method (the same applies below).

TABLE 1

| Primer | Sequence | Tm(° C.) | SEQ ID NO. |
|---|---|---|---|
| F1 Primer for UGT1A1*6 | 5'-gcagcagagggacatgaaata-3' | 56.2 | 2 |
| | 5'-cagcagagggacatgaaata-3' | 53.4 | 3 |
| | 5'-agcagagggacatgaaata-3' | 51.9 | 4 |
| | 5'-gcagagggacatgaaata-3' | 50.4 | 5 |
| | 5'-cagagggacatgaaata-3' | 46.7 | 6 |
| | 5'-ggggacatgaaatagttgtcctagcacctgacgc-3' | 65.9 | 74 |
| | 5'-gggacatgaaatagttgtcctagcacctgacgc-3' | 64.8 | 75 |
| | 5'-ggacatgaaatagttgtcctagcacctgacgc-3' | 63.6 | 76 |
| | 5'-gacatgaaatagttgtcctagcacctgacgc-3' | 62.4 | 77 |
| | 5'-acatgaaatagttgtcctagcacctgacgc-3' | 62 | 78 |
| | 5'-catgaaatagttgtcctagcacctgacgc-3' | 61.1 | 79 |
| | 5'-atgaaatagttgtcctagcacctgacgc-3' | 60.4 | 80 |
| | 5'-tgaaatagttgtcctagcacctgacgc-3' | 60.4 | 81 |
| | 5'-gaaatagttgtcctagcacctgacgc-3' | 59.3 | 82 |
| | 5'-aaatagttgtcctagcacctgacgc-3' | 58.7 | 83 |
| | 5'-aatagttgtcctagcacctgacgc-3' | 58.4 | 84 |
| | 5'-atagttgtcctagcacctgacgc-3' | 58.1 | 85 |
| | 5'-tagttgtcctagcacctgacgc-3' | 57.9 | 86 |
| | 5'-agttgtcctagcacctgacgc-3' | 58.3 | 87 |
| | 5'-gttgtcctagcacctgacgc-3' | 57.2 | 88 |
| | 5'-ttgtcctagcacctgacgc-3' | 56 | 89 |
| | 5'-tgtcctagcacctgacgc-3' | 55.4 | 90 |

TABLE 1-continued

| Primer | Sequence | Tm (° C.) | SEQ ID NO. |
|---|---|---|---|
| R1 Primer for UGT1A1*6 | 5'-ctcaaaaacattatgcccgagactaac-3' | 56.4 | 7 |
| | 5'-tcaaaaacattatgcccgagactaac-3' | 55.7 | 8 |
| | 5'-caaaaacattatgcccgagactaac-3' | 54.7 | 9 |
| | 5'-aaaaacattatgcccgagactaac-3' | 53.5 | 10 |
| | 5'-aaaacattatgcccgagactaac-3' | 53 | 11 |
| | 5'-aaacattatgcccgagactaac-3' | 52.4 | 12 |
| | 5'-aacattatgcccgagactaac-3' | 51.8 | 13 |
| | 5'-acattatgcccgagactaac-3' | 51.1 | 14 |
| | 5'-cattatgcccgagactaac-3' | 49.3 | 15 |
| | 5'-attatgcccgagactaac-3' | 47.4 | 16 |
| | 5'-ttatgcccgagactaac-3' | 46.6 | 17 |
| | 5'-ccgagactaacaaaagactctttcacatcctccctttgg-3' | 65 | 106 |
| | 5'-cgagactaacaaaagactctttcacatcctcccttggg-3' | 64 | 107 |
| | 5'-gagactaacaaaagactctttcacatcctcccttggg-3' | 62.7 | 108 |
| | 5'-agactaacaaaagactctttcacatcctcccttggg-3' | 62.4 | 109 |
| | 5'-gactaacaaaagactctttcacatcctcccttggg-3' | 61.8 | 110 |
| | 5'-actaacaaaagactctttcacatcctcccttggg-3' | 61.5 | 111 |
| | 5'-ctaacaaaagactctttcacatcctcccttggg-3' | 60.6 | 112 |
| | 5'-taacaaaagactctttcacatcctcccttggg-3' | 60.2 | 113 |
| | 5'-aacaaaagactctttcacatcctcccttggg-3' | 60.6 | 114 |
| | 5'-acaaaagactctttcacatcctcccttggg-3 | 60.4 | 115 |
| | 5'-caaaagactctttcacatcctcccttggg-3' | 59.4 | 91 |
| | 5'-aaaagactctttcacatcctcccttggg-3' | 58.7 | 116 |
| | 5'-aaagactctttcacatcctcccttggg-3' | 58.4 | 117 |
| | 5'-aagactctttcacatcctcccttggg-3' | 58.1 | 118 |
| | 5'-agactctttcacatcctcccttggg-3' | 57.8 | 119 |
| | 5'-gactctttcacatcctcccttggg-3' | 56.8 | 120 |
| | 5'-actctttcacatcctcccttggg-3' | 55.9 | 121 |
| | 5'-ctctttcacatcctcccttggg-3' | 54.5 | 122 |

Next, as described above, the primer set (2) is a primer set of a pair of primers including a forward primer composed of the following oligonucleotide (F2) and a reverse primer composed of the following oligonucleotide (R2): (F2): oligonucleotide that is at least one oligonucleotide having a sequence identical to that of a region extending from guanine (G) at base 2622 to be considered as the first base to any one of the 15$^{th}$ to 27$^{th}$ bases in the direction toward the 5' end in the UGT1A1 gene consisting of the base sequence of SEQ ID NO: 1, with the guanine (G) being the 3' end, and (R2): oligonucleotide that is at least one oligonucleotide complementary to a region extending from cytosine (C) at base 2687 to be considered as the first base to any one of the 17$^{th}$ to 26$^{th}$ bases in the direction toward the 3' end in the UGT1A1 gene consisting of the base sequence of SEQ ID NO: 1, with guanine (G) complementary to the cytosine (C) at base 2687 being the 3' end.

The primer set (2) is a primer set for amplifying a DNA strand including a region from base 2623 to base 2686 in SEQ ID NO: 1 as well as a strand complementary thereto. Base 2635 in this region (i.e. base 2635 in SEQ ID NO: 1) is known for the presence of a point mutation (2635C, 2635A) that affects the function of UGT1A1, and the polymorphism thereof is UGT1A1*27 described above. In the present invention, the polymorphism of this site can be indicated as 2635C/C or 26359A/A in the case of homozygote and as 2635C/A in the case of heterozygote. Hereinafter, this primer set (2) also may be referred to as a "primer set for UGT1A1*27". When only the polymorphism UGT1A1*27 is to be analyzed, it is sufficient to use only the primer set for UGT1A1*27.

For the same reason as that described with respect to the primer set (1), in the present invention, the F2 primer and the R2 primer of the primer set (2) can be any primers, as long as the base located at the 3' end that serves to determine the site from which DNA polymerase starts amplification satisfies the aforementioned condition. Accordingly, the length itself of the F2 primer and the R2 primer is not particularly limited and can be, for example, as described above. Specifically, it is preferable that the F2 primer be at least one oligonucleotide having a sequence identical to that of a region extending from guanine (G) at base 2622 to be considered as the first base to any one of the 15$^{th}$ to 27$^{th}$ bases (preferably the 16$^{th}$ to 27$^{th}$ bases and more preferably the 17$^{th}$ to 27$^{th}$ bases) in the direction toward the 5' end in the base sequence of SEQ ID NO: 1. Furthermore, it is preferable that the R2 primer be at least one oligonucleotide complementary to a region extending from cytosine (C) at base 2687 to be considered as the first base to any one of the 17$^{th}$ to 26$^{th}$ bases (preferably the 18$^{th}$ to 26$^{th}$ bases and more preferably the 19$^{th}$ to 26$^{th}$ bases) in the direction toward the 3' end in the base sequence of SEQ ID NO: 1. Since each 3' end of the F2 primer and the R2 primer is fixed, the region to be elongated from the primer is, for example, a region from base 2623 to base 2686 in SEQ ID NO: 1 as described above. However, the length of the whole amplification product obtained varies according to the length of the primer to be used.

Furthermore, it is not necessary for the R2 primer and the F2 primer to be oligonucleotides perfectly complementary to the base sequence indicated in SEQ ID NO: 1 and to the strand complementary to the base sequence, respectively. In other words, the part excluding the base located at the 3' end in each primer may be different in one to five bases from that of a perfectly complementary oligonucleotide.

Specific examples of the F2 primer and the R2 primer are indicated below but the present invention is not limited thereto. The combination of these F2 primer and R2 primer is not limited by any means. Specifically, however, a primer set (2') is particularly preferable, which includes a F2' primer composed of oligonucleotide of SEQ ID NO: 21 or SEQ ID NO: 92, and a R2' primer composed of oligonucleotide of SEQ ID NO: 29 or SEQ ID NO: 98.

TABLE 2

| Primer | Sequence | Tm (° C.) | SEQ ID NO. |
|---|---|---|---|
| F2 Primer for UGT1A1*27 | 5'-ccttttcacagaactttctgtgcgacg-3' | 60.5 | 92 |
|  | 5'-cttttcacagaactttctgtgcgacg-3' | 58.9 | 93 |
|  | 5'-ttttcacagaactttctgtgcgacg-3' | 58.3 | 94 |
|  | 5'-tttcacagaactttctgtgcgacg-3' | 58 | 95 |
|  | 5'-ttcacagaactttctgtgcgatg-3' | 57.7 | 96 |
|  | 5'-tcacagaactttctgtgcgacg-3' | 57.3 | 97 |
|  | 5'-cacagaactttctgtgcgacg-3' | 56.2 | 18 |
|  | 5'-acagaactttctgtgcgacg-3' | 55 | 19 |
|  | 5'-cagaactttctgtgcgacg-3' | 53.4 | 20 |
|  | 5'-agaactttctgtgcgacg-3' | 51.9 | 21 |
|  | 5'-gaactttctgtgcgacg-3' | 50.3 | 22 |
|  | 5'-aactttctgtgcgacg-3' | 48.7 | 23 |
|  | 5'-actttctgtgcgacg-3' | 47.6 | 24 |
| R2 Primer for UGT1A1*27 | 5'-gccagacagatgcagagctcaatagg-3' | 60.7 | 98 |
|  | 5'-ccagacagatgcagagctcaatagg-3' | 58.6 | 99 |
|  | 5'-cagacagatgcagagctcaatagg-3' | 56.7 | 25 |
|  | 5'-agacagatgcagagctcaatagg-3' | 55.7 | 26 |
|  | 5'-gacagatgcagagctcaatagg-3' | 54.5 | 27 |
|  | 5'-acagatgcagagctcaatagg-3' | 53.5 | 28 |
|  | 5'-cagatgcagagctcaatagg-3' | 51.9 | 29 |
|  | 5'-agatgcagagctcaatagg-3' | 50.3 | 30 |
|  | 5'-gatgcagagctcaatagg-3' | 48.7 | 31 |
|  | 5'-atgcagagctcaatagg-3' | 47 | 32 |

Next, as described above, the primer set (3) is a primer set of a pair of primers including a forward primer composed of the following oligonucleotide (F3) and a reverse primer composed of the following oligonucleotide (R3):

(F3): oligonucleotide that is at least one oligonucleotide having a sequence identical to that of a region extending from cytosine (C) at base 1863 to be considered as the first base to any one of the $17^{th}$ to $31^{st}$ bases in the direction toward the 5' end in the UGT1A1 gene consisting of the base sequence of SEQ ID NO: 1, with the cytosine (C) being the 3' end, and (R3): oligonucleotide that is at least one oligonucleotide complementary to a region extending from cytosine (C) at base 1928 to be considered as the first base to any one of the $16^{st}$ to $20^{th}$ bases in the direction toward the 3' end in the UGT1A1 gene consisting of the base sequence of SEQ ID NO: 1, with guanine (G) complementary to the cytosine (C) at base 1928 being the 3' end.

The primer set (3) is a primer set for amplifying a DNA strand including a region from base 1864 to base 1927 in SEQ ID NO: 2 as well as a strand complementary thereto. In this region, a mutation (six repeated TAs, seven repeated TAs) in the TATA box starting at base 1895 of SEQ ID NO: 1 is known as a point mutation that affects the function of UGT1A1, and the polymorphism thereof is UGT1A1*28 described above. In the present invention, the polymorphism of this site can be indicated as 1895-TA7/TA7 or 1895-TA6/TA6 in the case of homozygote and as 1859-TA6/TA7 in the case of heterozygote. SEQ ID NO: 1 is a sequence of the polymorphism UGT1A1*28 having seven repeated TAs. Hereinafter, this primer set (3) also may be referred to as a "primer set for UGT1A1*28". When only the polymorphism UGT1A1*28 is to be analyzed, it is sufficient to use only the primer set for UGT1A1*28.

In the present invention, from the same reason as that described with respect to the primer set (1), the F3 primer and the R3 primer of the primer set (3) can be any primers as long as the base located at the 3' end that serves to determine the site from which DNA polymerase starts amplification satisfies the aforementioned condition. Accordingly, the length itself of the F3 primer and the R3 primer is not particularly limited and can be, for example, as described above. Specifically, it is preferable that the F3 primer be at least one oligonucleotide having a sequence identical to that of a region extending from cytosine (C) at base 1863 to be considered as the first base to any one of the $17^{th}$ to $31^{st}$ bases (preferably the $18^{th}$ to $28^{th}$ bases and more preferably the $19^{th}$ to $24^{th}$ bases) in the direction toward the 5' end in the base sequence of SEQ ID NO: 1. Furthermore, it is preferable that the R3 primer be at least one oligonucleotide complementary to a region extending from cytosine (C) at base 1928 to be considered as the first base to any one of the $16^{th}$ to $20^{th}$ bases (preferably the $17^{th}$ to $20^{th}$ bases and more preferably the $17^{th}$ to $19^{th}$ bases) in the direction toward the 3' end in the base sequence of SEQ ID NO: 1. Since each 3' end of the F3 primer and the R3 primer is fixed, the region to be elongated from the primer is, for example, a region from base 1864 to base 1927 in SEQ ID NO: 2 as described above. However, the length of the whole amplification product obtained varies according to the length of the primer to be used.

Furthermore, it is not necessary for the R3 primer and the F3 primer to be oligonucleotides perfectly complementary to the base sequence indicated in SEQ ID NO: 1 and to the strand complementary to the base sequence, respectively. In other words, the part excluding the base located at the 3' end in each primer may be different in one to five bases from that of a perfectly complementary oligonucleotide.

Specific examples of the F3 primer and the R3 primer are indicated below but the present invention is not limited thereto. The combination of these F3 primer and R3 primer is not limited by any means. Specifically, however, a primer set (3') is particularly preferable, which includes a F2' primer composed of oligonucleotide of SEQ ID NO: 42 or SEQ ID NO: 123 and a R3' primer composed of oligonucleotide of SEQ ID NO: 46 or SEQ ID NO: 48.

TABLE 3

| Primer | Sequence | Tm(° C.) | SEQ ID NO. |
|---|---|---|---|
| F3 Primer for UGT1A1*28 | 5'-agcttttatagtcacgtgacacagtcaaac-3' | 59.5 | 123 |
| | 5'-gcttttatagtcacgtgacacagtcaaac-3' | 58.7 | 124 |
| | 5'-cttttatagtcacgtgacacagtcaaac-3' | 56.8 | 33 |
| | 5'-ttttatagtcacgtgacacagtcaaac-3' | 56.1 | 34 |
| | 5'-tttatagtcacgtgacacagtcaaac-3' | 55.8 | 35 |
| | 5'-ttatagtcacgtgacacagtcaaac-3' | 55.4 | 36 |
| | 5'-tatagtcacgtgacacagtcaaac-3' | 55 | 37 |
| | 5'-tatagtcacgtgacacagtcaaac-3' | 54.5 | 38 |
| | 5'-atagtcacgtgacacagtcaaac-3' | 54.8 | 39 |
| | 5'-tagtcacgtgacacagtcaaac-3' | 54.5 | 40 |
| | 5'-agtcacgtgacacagtcaaac-3' | 54.8 | 41 |
| | 5'-gtcacgtgacacagtcaaac-3' | 53.5 | 42 |
| | 5'-tcacgtgacacagtcaaac-3' | 52.1 | 43 |
| | 5'-cacgtgacacagtcaaac-3' | 50.6 | 44 |
| | 5'-acgtgacacagtcaaac-3' | 48.7 | 45 |
| R3 Primer for UGT1A1*28 | 5'-cgcctttgctcctgccagag-3' | 59.9 | 46 |
| | 5'-gcctttgctcctgccagag-3' | 57.3 | 47 |
| | 5'-cctttgctcctgccagag-3' | 54.1 | 48 |
| | 5'-ctttgctcctgccagag-3' | 51.3 | 49 |
| | 5'-tttgctcctgccagag-3' | 49.7 | 50 |

Furthermore, each primer of the aforementioned primer sets (1) to (3) may be, for example, one with the 5' end to which any conventionally known sequence has been added in order to increase the amplification reaction temperature.

Preferably, a primer set for amplifying the UGT1A1 gene of the present invention including at least one of the aforementioned primer sets (1) to (3) is used, for example, in amplifying the UGT1A1 gene in a biological sample such as a whole blood sample. Particularly, when the primer set for amplifying the UGT1A1 gene of the present invention is used in combination with a probe for detecting a polymorphism as described later, it is preferable that the ratio of the whole blood sample to be added to the reaction solution for amplifying a gene be 0.1 to 0.5 vol %. This will be described later.

<Reagent for Amplifying UGT1A1 Gene>

As described above, a reagent for amplifying the UGT1A1 gene of the present invention is a reagent for amplifying the UGT1A1 gene by a gene amplification method, wherein the reagent includes a primer set for amplifying the UGT1A1 gene of the present invention. The reagent for amplifying the UGT1A1 gene of the present invention is characterized by including a primer set of the present invention and, for example, components other than this are not limited by any means.

For example, in order to detect an amplification product obtained by a gene amplification method in which a primer set of the present invention is used, the reagent for amplifying the UGT1A1 gene of the present invention further may include a probe that can hybridize to a site to be detected in the UGT1A1 gene. As described above, the primer set for amplifying the UGT1A1 gene of the present invention allows amplification products of one to three target regions in the UGT1A1 gene to be obtained by a gene amplification method according to, for example, the type of the primer sets (1) to (3) included therein. Accordingly, when a probe complementary to the sequence to be detected in each target region described above is allowed to coexist, for example, the presence or absence of amplification or the genotype (polymorphism) of the site to be detected can be detected by the method described later. Such probes and the method of using them are explained later in the description of the polymorphism analysis method. Furthermore, it is preferable that the reagent for amplifying the UGT1A1 gene of the present invention be used in amplifying the UGT1A1 gene in a biological sample such as whole blood. Particularly, when the reagent for amplifying the UGT1A1 gene of the present invention is used in combination with the probe described above, it is preferable that the ratio of the whole blood sample to be added to the reaction solution for amplifying a gene be 0.1 to 0.5 vol %. In the present invention, the term "sequence to be detected" denotes a sequence including a site (site to be detected) at which a polymorphism is generated.

The form of the reagent for amplifying the UGT1A1 gene of the present invention is not particularly limited and it may be, for example, a liquid reagent containing a primer set for amplifying the UGT1A1 gene of the present invention or a dry reagent that is to be suspended in a solvent before use. Furthermore, the content of the primer set for amplifying the UGT1A1 gene also is not particularly limited.

<Method of Manufacturing Amplification Product>

As described above, the method of manufacturing an amplification product of the present invention is a method of manufacturing an amplification product of the UGT1A1 gene by a gene amplification method, wherein the method includes the following step (I):

(I) amplifying the UGT1A1 gene in a reaction solution using a primer set for amplifying the UGT1A1 gene of the present invention, with nucleic acid contained in a sample being used as a template.

When a primer set for amplifying the UGT1A1 gene of the present invention is used to perform an amplification reaction in this manner, the target region of the UGT1A1 gene can be amplified as described above. Furthermore, when the primer set for amplifying the UGT1A1 gene of the present invention includes two of the primer sets (1) to (3), two target regions including two sites to be detected, respectively, in the UGT1A1 gene can be amplified simultaneously in the same reaction solution. Moreover, when the primer set for amplifying the UGT1A1 gene of the present invention includes all the primer sets (1) to (3), three target regions including three sites to be detected, respectively, in the UGT1A1 gene can be amplified simultaneously in the same reaction solution. The target regions to be amplified according to the present invention are regions including the sites to be detected at which respective polymorphisms (UGT1A1*28, UGT1A1*6, and UGT1A1*27) are generated, respectively, as described above. The method of manufacturing an amplification product of the present invention is characterized in that a primer set of the present invention is used, and, for example, the type of and conditions for the gene amplification method are not limited by any means.

The gene amplification method is not particularly limited as described above. Examples thereof include the polymerase chain reaction (PCR) method, a nucleic acid sequence based amplification (NASBA) method, a transcription-mediated amplification (TMA) method, and a strand displacement amplification (SDA) method. Particularly, the PCR method is preferable. The present invention is described below using the PCR method as an example but is not limited thereby.

The sample to which the present invention is to be applied is not particularly limited as long as it contains, for example, nucleic acid to serve as a template. However, it is preferable that the present invention be applied to, for example, a contaminated sample. Examples of the contaminated sample include whole blood, cells in the mouth (for example, oral mucosa), somatic cells of nails and hairs, germ cells, expectoration, amniotic fluid, paraffin-embedded tissue, urine, gastric juice (for example, gastric lavage fluid), and suspensions thereof. According to the method of manufacturing an amplification product using a primer set of the present invention, for example, even in the case of a sample (particularly, a biological sample such as whole blood or cells in the mouth) with various contaminants, the method is less subject to the effect thereof and allows the target region in the UGT1A1 gene to be amplified specifically. Thus, according to the present invention, even a highly contaminated sample, which is difficult to use in the conventional methods, can be used as it is, for instance, without being pretreated, for example, without being purified. Therefore, it can be said that an amplification product can be prepared quicker as compared to the conventional method also from the viewpoint of the pretreatment of the sample.

The ratio of the sample to be added to the reaction solution is not particularly limited. Specifically, when the sample is a biological sample (for example, a whole blood sample), the lower limit of the ratio thereof to be added to the reaction solution is, for example, preferably at least 0.01 vol %, more preferably at least 0.05 vol %, and further preferably at least 0.1 vol %. Furthermore, the upper limit of the ratio thereof to be added also is not particularly limited and is, for example, preferably 2 vol % or lower, more preferably 1 vol % or lower, and further preferably 0.5 vol % or lower.

When an optical detection to be described later is intended to be performed, particularly, when an optical detection is performed using a labeled probe, it is preferable that the ratio of a biological sample, such as a whole blood sample, to be added to the reaction solution be set at, for example, 0.1 to 0.5 vol %. Generally, in the PCR reaction, a heat treatment is carried out to denature DNA (i.e. to dissociate it into a single-stranded DNA). This heat treatment may denature, for example, sugar or protein contained in the sample and thereby may generate an insolubilized precipitate or turbidity. Therefore, when the presence or absence of an amplification product or the genotype (polymorphism) of a site to be detected is to be checked by an optical method, the generation of such a precipitate or turbidity may affect the measurement accuracy. However, when the ratio of the whole blood sample to be added to the reaction solution is set in the range described above, for example, an effect caused by generation of, for example, a precipitate due to denaturation can be prevented sufficiently and thereby the accuracy of measurement carried out by the optical method can be improved, although the mechanism thereof is unknown. Furthermore, since it also can sufficiently prevent PCR from being inhibited due to the contaminants contained in a whole blood sample, the amplification efficiency can be improved further. Accordingly, when in addition to the use of a primer set of the present invention, the ratio of the sample such as a whole blood sample to be added is set in the aforementioned range, the need to pretreat the sample additionally can be omitted.

Furthermore, the ratio of the whole blood sample in the reaction solution can be indicated not in the aforementioned volume ratio (for example, 0.1 to 0.5 vol %) but in a weight ratio of hemoglobin (hereinafter referred to as "Hb"). In this case, the ratio of the whole blood sample in the reaction solution is, for example, preferably in the range of 0.565 to 113 g/L, more preferably in the range of 2.825 to 56.5 g/L, and further preferably in the range of 5.65 to 28.25 µg/L, in terms of the amount of Hb. The ratio of the whole blood sample to be added during the reaction may satisfy, for example, both the volume ratio and the Hb weight ratio, or one of them.

The whole blood may be any one of, for example, hemolyzed whole blood, unhemolyzed whole blood, anticoagulated whole blood, and whole blood containing coagulated fractions.

In the present invention, the target nucleic acid contained in a sample is, for example, DNA. The aforementioned DNA may be DNA contained originally in the sample, such as a biological sample, or an amplification product DNA obtained through amplification by a gene amplification method. In the latter case, an example thereof is cDNA that is generated from RNA (for example, total RNA or mRNA) contained originally in the sample by a reverse transcription reaction (for instance, reverse transcription PCR (RT-PCR)).

In the method of manufacturing an amplification product of the present invention, it is preferable that albumin further be added to the reaction solution before the start of a gene amplification reaction. Such addition of albumin further can reduce the effect of generation of a precipitate or turbidity described above and also further can improve the amplification efficiency. Specifically, it is preferable that albumin be added before the amplification reaction in step (I) or a step of dissociation into a single-stranded DNA.

The ratio of albumin to be added to the reaction solution is, for example, in the range of 0.01 to 2 wt %, preferably 0.1 to 1 wt %, and more preferably 0.2 to 0.8 wt %. The albumin is not particularly limited. Examples thereof include bovine serum albumin (BSA), human serum albumin, rat serum albumin, and horse serum albumin. One of them may be used or two or more of them may be used in combination.

Next, a method of manufacturing an amplification product of the present invention is described using an example in which with respect to a whole blood sample including DNA as target nucleic acid, amplification products of three target regions of the UGT1A1 gene are produced by PCR using primer sets for amplifying the UGT1A1 gene of the present invention including the aforementioned primer sets (1) to (3). The present invention is characterized by using primer sets of the present invention and other configurations and conditions are not limited by any means.

First, a PCR reaction solution is prepared. The ratio of the primer sets of the present invention to be added is not particularly limited. However, it is preferable that F primers of the primer sets (1) to (3) each be added to be 0.1 to 2 µmol/L, more preferably 0.25 to 1.5 µmol/L, and particularly preferably 0.5 to 1 µmol/L. Furthermore, it is preferable that R primers of the primer sets (1) to (3) each be added to be 0.1 to 2 µmol/L, more preferably 0.25 to 1.5 µmol/L, and particularly preferably 0.5 to 1 µmol/L. The ratio (F:R, molar ratio) between the F primer and the R primer to be added to each primer set is not particularly limited. It is, for example, preferably 1:0.25 to 1:4 and more preferably 1:0.5 to 1:2.

The ratio of the whole blood sample in the reaction solution is not particularly limited but is preferably in the range described above. The whole blood sample may be added to the reaction solution without being treated or may be added to the reaction solution after being diluted with a solvent such as water or a buffer solution beforehand. When the whole blood sample is diluted beforehand, the dilution ratio is not particularly limited. It can be set so that, for example, the final ratio of the whole blood added to the reaction solution is in the aforementioned range, for example, 1:100 to 1:2000 and preferably 1:200 to 1:1000.

Other composition components in the reaction solution are not particularly limited and can be conventionally known components, whose ratios also are not particularly limited. Examples of the composition components include DNA polymerase, nucleotide (nucleoside triphosphate (dNTP)), and a solvent. Furthermore, as described above, it is preferable that the reaction solution further contain albumin. In the reaction solution, the order of addition of the respective composition components is not limited by any means.

The DNA polymerase is not particularly limited and, for example, a conventionally known thermoduric bacteria-derived polymerase can be used. Specifically, for example, *Thermus aquaticus*-derived DNA polymerase (U.S. Pat. Nos. 4,889,818 and 5,079,352) (trade name: Taq polymerase), *Thermus thermophilus*-derived DINA polymerase (WO 91/09950) (rTth DNA polymerase), *Pyrococcus furiosus*-derived DNA polymerase (WO 92/9688) (Pfu DNA polymerase; manufactured by Stratagenes), and *Thermococcus litoralis*-derived DNA polymerase (EP-A 455 430) (Trademark: Vent; manufactured by Biolab New England) are commercially available. Particularly, *Thermus aquaticus*-derived thermostable DNA polymerase is preferable.

The ratio of DNA polymerase to be added to the reaction solution is not particularly limited and is, for example, 1 to 100 U/mL, preferably 5 to 50 U/mL, and more preferably 20 to 30 U/mL. With respect to the unit of activity (U) of DNA polymerase, generally, 1 U denotes the activity that allows all 10 nmol of nucleotide to be taken into an acid-insoluble precipitate in 30 minutes at 74° C. in a reaction solution for activity measurement, with an activated salmon sperm DNA being used as a template primer. The composition of the reaction solution for activity measurement is, for example, 25 mM TAPS buffer (pH 9.3, 25° C.), 50 mM KCl, 2 mM MgCl$_2$, 1 mM mercaptoethanol, 200 μM dATP, 200 μM dGTP, 200 μM dTTP, 100 μM [α-$^{32}$P] dCTP, and 0.25 mg/mL activated salmon sperm DNA.

Generally, examples of the nucleoside triphosphate include dNTP (dATP, dCTP, dTTP). The ratio of dNTP to be added to the reaction solution is not particularly limited and is, for example, 0.01 to 1 mmol/L, preferably 0.05 to 0.5 mmol/L, and more preferably 0.1 to 0.3 mmol/L.

Examples of the solvent include buffer solutions such as Tris-HCl, Tricine, MES, MOPS, HEPES, and CAPS. Commercially available PCR buffer solutions or buffer solutions of commercially available PCR kits can be used.

Furthermore, the PCR reaction solution further may contain heparin, betaine, KCl, MgCl$_2$, MgSO$_4$, glycerol, etc. The ratios thereof to be added can be set in ranges in which the PCR reaction is not inhibited.

The total volume of the reaction solution is not particularly limited and can be determined suitably according to, for example, the equipment (thermal cycler) to be used. It is generally 1 to 500 μL and preferably 10 to 100 μL.

Subsequently, PCR is performed. The cycle conditions in PCR are not particularly limited, and, for example, (1) dissociation of whole blood-derived double-stranded DNA into single-stranded DNA, (2) annealing of a primer, and (3) elongation of a primer (polymerase reaction) are as described below. Furthermore, the number of cycles also is not particularly limited but preferably is at least 30, with the following three steps (1) to (3) being considered as one cycle. The upper limit thereof in total, is not particularly limited and, for example, is 100 cycles or less, preferably 70 cycles or less, and further preferably 50 cycles or less. The change in temperature in each step can be controlled automatically using, for example, a thermal cycler. When primer sets of the present invention are used, since they are excellent in amplification efficiency as described above, 50 cycles can be completed in approximately one hour (preferably within one hour) according to the present invention, while it takes approximately three hours to complete 50 cycles according to the conventional methods.

TABLE 4

| | Temperature (° C.) and Time (sec) |
|---|---|
| (1) Dissociation of single-stranded DNA | For example, 90 to 99° C., 1 to 120 sec<br>Preferably, 92 to 95° C., 1 to 60 sec |
| (2) Annealing of primer | For example, 40 to 70° C., 1 to 300 sec<br>Preferably, 50 to 70° C., 5 to 60 sec |
| (3) Elongation reaction | For example, 50 to 80° C., 1 to 300 sec<br>Preferably, 50 to 75° C., 5 to 60 sec |

In the manner described above, amplification products complementary to the three target regions in the UGT1A1 gene can be produced. When an amplification product complementary to one or those complementary to two of the three target regions are to be produced, a primer set for amplifying the UGT1A1 gene of the present invention containing one or two of the primer sets (1) to (3) corresponding to the target region(s) can be used.

The method of manufacturing an amplification product of the present invention further may include a step of detecting an amplification product of a target region obtained by the aforementioned amplification reaction. This makes it possible to detect the presence or absence of the amplification product or the genotype (polymorphism, UGT1A1*6, UGT1A1*27, or UGT1A1*28) in the target region in the UGT1A1 gene. The presence or absence of the amplification product can be checked by a conventionally known method. Specifically, it can be checked by, for example, further adding a probe (for instance, a fluorescently-labeled probe) that can hybridize to a site to be detected in the UGT1A1 gene to the reaction solution in step (I), and further in step (II), measuring the fluorescence intensity of the fluorescent label in the probe with respect to the reaction solution. Furthermore, when two or three target regions are to be amplified, it can be checked by, for example, further adding two or three probes (for instance, fluorescently-labeled probes) that can hybridize to the respective sites to be detected in the UGT1A1 gene to the reaction solution in step (I), and further in step (II), measuring the fluorescence intensity of the fluorescent label in each probe with respect to the reaction solution. Detection of polymorphisms, UGT1A1*6, UGT1A1*27, and UGT1A1*28, in the UGT1A1 gene is described below as an embodiment of the present invention.

<UGT1A1 Gene Polymorphism Analysis Method>

A UGT1A1 gene polymorphism analysis method of the present invention is a method of analyzing the polymorphism of a site to be detected in the UGT1A1 gene, wherein the method includes the following steps (i) to (iv):

(i) amplifying a region including a site to be detected in the UGT1A1 gene in a reaction solution by a method of manufacturing an amplification product according to the present invention, (ii) preparing a reaction solution that contains the amplification product obtained in step (i) and a probe capable of hybridizing to the site to be detected, (iii) measuring signal values that indicate melting states of a hybridization product between the amplification product and the probe while changing the temperature of the reaction solution, and (iv) determining a polymorphism of the site to be detected from a change in the signal values accompanying a change in the temperature.

In this manner, when an amplification product is produced using a primer set for amplifying the UGT1A1 gene of the present invention, it is possible to amplify the target region including a site to be detected of a polymorphism (UGT1A1*6, UGT1A1*27, or UGT1A1*28) in the UGT1A1 gene as described above and to analyze the polymorphism of the site to be detected in the target region.

The probe to be used in step (ii) is not particularly limited. Examples thereof include a probe that hybridizes to the site where the polymorphism UGT1A1*6 is generated (hereinafter, also referred to as a "probe for UGT1A1*6"), a probe that hybridizes to the site where the polymorphism UGT1A1*27 is generated (hereinafter, also referred to as a "probe for UGT1A1*27"), and a probe that hybridizes to the site where the polymorphism UGT1A1*28 is generated (hereinafter, also referred to as a "probe for UGT1A1*28"). Preferably, these probes each are a probe complementary to a sequence to be detected containing the aforementioned sequence to be detected. Any one of those probes may be used or two or all three of them may be used. This can be determined, for example, according to the type of the target region(s) amplified with a primer set for amplifying the UGT1A1 gene of the present invention. When two or three probes are used, for example, the polymorphisms of two sites to be detected or all the three sites to be detected can be analyzed using the same reaction solution.

The probes for detecting the polymorphisms are not particularly limited and can be configured by a conventionally known method. For instance, they each may be designed as a sequence to be detected containing a site to be detected of a polymorphism, based on the sequence of a sense strand or the sequence of an antisense strand of the UGT1A1 gene. Furthermore, the base located at the site to be detected of a polymorphism can be determined suitably according to the type of each polymorphism. In other words, in the case of UGT1A1*6, since the polymorphisms of "G" and "A" at base 2160 in SEQ ID NO: 1 have been known, examples of the probe include a probe complementary to either a sequence to be detected including G at base 2160 or a sequence to be detected including A at base 2160 (a probe for detecting a sense strand), and a probe complementary to a sequence of an antisense strand thereof (a probe for detecting an antisense strand). Furthermore, in the case of UGT1A1*27, since the polymorphisms of "C" and "A" at base 2635 in SEQ ID NO: 1 have been known, examples of the probe include a probe complementary to either a sequence to be detected including C at base 2635 or a sequence to be detected including A at base 2635 (a probe for detecting a sense strand), and a probe complementary to a sequence of an antisense strand thereof (a probe for detecting an antisense strand). Moreover, in the case of UGT1A1*28, since the polymorphisms of "six repeated TAs: TA6" and "seven repeated TAs: TA7" have been known in the bases of the TATA box starting at base 1895 in SEQ ID NO: 1, examples of the probe include a probe complementary to either a sequence to be detected including six TAs repeated from base 1895 or a sequence to be detected including seven TAs repeated from base 1895 (a probe for detecting a sense strand), and a probe complementary to a sequence of an antisense strand thereof (a probe for detecting an antisense strand). As described above, when a probe is designed, with the base located at the site to be detected where a polymorphism is generated being set to be any one of the bases as described above, it is also possible to judge what type of polymorphism is expressed at each site to be detected in an UGT1A1 gene by the method as described later.

The probe can be added to an amplified reaction solution after step (i) i.e. after a target region in the UGT1A1 gene is subjected to an amplification reaction. However, it is preferable that the probe be added to a reaction solution before the amplification reaction in step (i) since this allows analysis to be performed easily and quickly.

The ratio of the probe to be added to the reaction solution is not particularly limited. For example, each probe is added to be preferably in the range of 10 to 400 nmol and more preferably in the range of 20 to 200 nmol. When a fluorescent dye is used as the label for a probe, an unlabeled probe with a sequence identical to that of the labeled probe may be used in combination with the labeled probe, for example, in order to adjust the fluorescence intensity to be detected, and the unlabeled probe may include a phosphate group added to the 3' end thereof. In this case, the molar ratio between the labeled probe and the unlabeled probe is preferably, for example, 1:10 to 10:1. The length of the probe is not particularly limited. It is, for example, 5- to 50-mers and preferably 10- to 30-mers.

The Tm value is described. When a solution containing double-stranded DNA is heated, the absorbance at 260 nm increases. This is because heating releases the hydrogen bonds between both strands in the double-stranded DNA to dissociate it into single-stranded DNA (i.e. DNA melting). When all double-stranded DNAs are dissociated into single-stranded DNAs, the absorbance thereof indicates approximately 1.5 times that obtained at the start of heating (i.e. absorbance of only double-stranded DNAs), which makes it possible to judge that melting is completed thereby. Based on this phenomenon, the melting temperature Tm generally is defined as a temperature at which the absorbance has reached 50% of the total increase in absorbance.

In the aforementioned step (iii), the measurement of the signal values that indicate the melting states of the hybridization product between the amplification product and the probe may be a measurement of absorbance at 260 nm as described above but may be a measurement of the signal of a labeling substance. Specifically, it is preferable that a labeled probe labeled with a labeling substance be used as the aforementioned probe to perform the measurement of the signal of the labeling substance. The labeled probe can be, for example, a labeled probe that exhibits a signal independently but does not exhibit a signal after hybridization, or a labeled probe that does not exhibit a signal independently but exhibits a signal after hybridization. The former probe does not exhibit a signal after forming a hybrid (double-stranded DNA) with a sequence to be detected but exhibits a signal when the probe is released by heating. On the other hand, the latter probe exhibits a signal after forming a hybrid (double-stranded DNA) with a sequence to be detected but the signal is reduced (quenched) when the probe is released by heating. Accordingly, when the signal exhibited by the label is detected under a condition (absorption wavelength etc.) specific to the signal, the progress of melting of the hybridization product and the Tm value can be determined as in the case of the measurement of absorbance at 260 nm.

In the present invention, as described above, it is also possible to check polymorphisms with respect to amplification products of two or three target regions amplified in the same reaction solution. Accordingly, when two or three types of probes are used, it is preferable that they be labeled with different labels each of which is detected under its own condition. The use of different labels as described above makes it possible to analyze each amplification product separately by changing the detection conditions even in the same reaction solution.

Specific examples of labeling substances in the labeled probes include a fluorescent dye (fluorophore). A specific example of the labeled probes is preferably a probe that, for example, has been labeled with a fluorescent dye, exhibits fluorescence independently, and allows fluorescence to be reduced (for example, quenched) after hybridization. Generally, a probe that utilizes such a fluorescence quenching phenomenon is referred to as a fluorescence quenching probe. Particularly, with respect to the aforementioned probe, it is preferable that the 3' end or 5' end of oligonucleotide be labeled with a fluorescent dye and the base located at the end to be labeled be C. In this case, in the sequence to be detected, to which the labeled probe hybridizes, it is preferable that the base sequence of the labeled probe be designed so that the base to be paired with the end base C of the labeled probe or the base located 1 to 3 bases apart from the base to be paired be G. Generally, such a probe is referred to as a guanine quenching probe and is known as so-called QProbe (registered trademark). When such a guanine quenching probe hybridizes to a sequence to be detected, C located at the end, which has been labeled with a fluorescent dye, approaches G in the DNA to be detected, and thereby a phenomenon occurs in which the emission of the fluorescent dye decreases (the fluorescence intensity decreases). The use of such a probe makes it possible to verify hybridization and dissociation easily according to a change in the signal.

The fluorescent dye is not particularly limited. Examples thereof include fluorescein, phosphor, rhodamine, and polymethine dye derivative. Examples of commercially available fluorescent dye include BODIPY FL (brand name, manufactured by Molecular Probe Inc.), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), and TAMRA (manufactured by Molecular Probe Inc.). The combination of fluorescent dyes to be used for a plurality of probes is not particularly limited as long as, for example, it allows the respective probes to be detected under different conditions. Examples thereof include a combination of Pacific Blue (with a detection wavelength is 450 to 480 nm), TAMRA (with a detection wavelength is 585 to 700 nm), and BODIPY FL (with a detection wavelength is 515 to 555 nm).

Specific examples of the sequences of probes for detecting the polymorphisms, UGT1A1*6, UGT1A1*27, and UGT1A1*28, are indicated below, but the present invention is not limited thereto. The following probe (1) is an example of the probe for UGT1A1*6 and is a probe for detecting an antisense strand. The following probe (2) is an example of the probe for UGT1A1*27, the following probe (2-1) is a probe for detecting an antisense strand and the following probe (2-2) is a probe for detecting a sense strand. Furthermore, the following probe (3) is an example of the probe for UGT1A1*28 and is a probe for detecting an antisense strand.

Probe (1)

Oligonucleotide that is at least one oligonucleotide having a sequence identical to that of a region extending from cytosine (C) at base 2173 to be considered as the first base to any one of the $17^{th}$ to $25^{th}$ bases in the direction toward the 5' end in SEQ ID NO: 1, with the cytosine being the 3' end.

Probe (2)

At least one oligonucleotide selected from:

(2-1) Oligonucleotide that is at least one oligonucleotide having a sequence identical to that of a region extending from cytosine (C) at base 2645 to be considered as the first base to any one of the $15^{th}$ to $22^{nd}$ bases in the direction toward the 5' end in SEQ ID NO: 1, with the cytosine being the 3' end, and (2-2) Oligonucleotide that is at least one oligonucleotide complementary to a region extending from guanine (G) at base 2625 to be considered as the first base to any one of the $17^{th}$ to $22^{nd}$ bases in the direction toward the 3' end in SEQ ID NO: 1, with cytosine (C) complementary to the guanine being the 3' end.

Probe (3)

Oligonucleotide that is at least one oligonucleotide having a sequence identical to that of a region extending from cytosine (C) at base 1892 to be considered as the first base to any one of the $25^{th}$ to $31^{st}$ bases in the direction toward the 3' end in SEQ ID NO: 1, with the cytosine being the 3' end.

In the probe (1), base 2160 in SEQ ID NO: 1 is indicated with "r", and the "r" is G or A. In the probe (2-1), base 2635 in SEQ ID NO: 1 is indicated with "m", and the "m" is C or A. In the probe (2-2), the base complementary to base 2635 in SEQ ID NO: 1 is indicated with "k", and the "k" is G or T. In the probe (3), the region corresponding to the TATA box starting at base 1895 in SEQ ID NO: 1 is seven repeated TAs or six repeated TAs.

Specific examples of Probe (1), Probe (2), and Probe (3) are indicated in the following table. "Tm(° C.)" indicated below in the table is Tm(° C.) obtained when each sequence indicated below in the table was hybridized with the sequence perfectly complementary thereto. The "Tm(° C.)" is a value calculated by using MELTCALC software (meltcalc.com/), with parameters including an oligonucleotide concentration of 0.2 µM and a sodium equivalent (Na eq.) of 50 mM.

TABLE 5

| Probe | Sequence | Tm(° C.) | SEQ ID NO. |
|---|---|---|---|
| Probe (1) for UGT1A1*6 | 5'-catcagagacAgagcattttacac-3' | 53.7 | 51 |
| | 5'-atcagagacAgagcattttacac-3' | 52.4 | 52 |
| | 5'-tcagagacAgagcattttacac-3' | 52.1 | 53 |
| | 5'-cagagacAgagcattttacac-3' | 50.7 | 54 |
| | 5'-agagacAgagcattttacac-3' | 49.1 | 55 |
| | 5'-gagacAgagcattttacac-3' | 47.6 | 56 |
| | 5'-agacAgagcattttacac-3' | 45.6 | 57 |
| | 5'-gacAgagcattttacac-3' | 44.1 | 58 |

TABLE 5-continued

| Probe | Sequence | Tm(° C.) | SEQ ID NO. |
|---|---|---|---|
| Probe (2) | 5'-tggtttattcccAgtatgcaacc-3' | 53.2 | 59 |
| for UGT1A1*27 | 5'-ggtttattcccAgtatgcaacc-3' | 50.9 | 60 |
|  | 5'-tttattcccAgtatgcaacc-3' | 49.3 | 61 |
|  | 5'-ttattcccAgtatgcaacc-3' | 48.5 | 62 |
|  | 5'-tattcccAgtatgcaacc-3' | 47.5 | 63 |
|  | 5'-attcccAgtatgcaacc-3' | 47.5 | 64 |
|  | 5'-ttcccAgtatgcaacc-3' | 46.5 | 65 |
|  | 5'-tcccAgtatgcaacc-3' | 45.4 | 66 |
|  | 5'-gggttgcatacTgggaataaac-3' | 53.2 | 100 |
|  | 5'-ggttgcatacTgggaataaac-3' | 50.9 | 101 |
|  | 5'-gttgcatacTgggaataaac-3' | 48.4 | 102 |
|  | 5'-ttgcatacTgggaataaac-3' | 46.4 | 103 |
|  | 5'-tgcatacTgggaataaac-3' | 45.5 | 104 |
|  | 5'-gcatacTgggaataaac-3' | 43.2 | 105 |
| Probe (3) | 5'-ccaTATATATATATATAtaagtaggagaggg-3' | 49.5 | 67 |
| for UGT1A1*28 | 5'-ccaTATATATATATATAtaagtaggagagg-3' | 47.7 | 68 |
|  | 5'-ccaTATATATATATATAtaagtaggagag-3' | 45.8 | 69 |
|  | 5'-ccaTATATATATATATAtaagtaggaga-3' | 44.6 | 70 |
|  | 5'-ccaTATATATATATATAtaagtaggag-3' | 43.3 | 71 |
|  | 5'-ccaTATATATATATATAtaagtagga-3' | 41.9 | 72 |
|  | 5'-ccaTATATATATATATAtaagtagg-3' | 40.5 | 73 |

Each probe (1) indicated in the above table consists of a sequence identical to that of a region having A at base 2160 in SEQ ID NO: 1, and the capitalized base indicates base 2160 in SEQ ID NO: 1. In each probe (1), the capitalized base can be replaced by "r", and the "r" may be either A or G. In the following table, the probes (2-1) that are expressed with SEQ ID NOs. 59 to 66 each consist of a sequence identical to that of a region having A at base 2635 in SEQ ID NO: 1, and the capitalized base indicates base 2635 in SEQ ID NO: 1. In each probe (2-1), the capitalized base can be replaced by "m", and the "m" may be either A or C. In the following table, the probes (2-2) that are expressed with SEQ ID NOs: 100 to 105 each consist of a sequence complementary to a region having A at base 2635 in SEQ ID NO; 1, and the capitalized base indicates the base complementary to base 2635 in SEQ ID NO: 1. In each probe (2-2), the capitalized base can be replaced by "k", and the "k" may be either T or G. Each probe (3) indicated in the following table consists of a sequence identical to that of a region having seven repeated TAs as the TATA box starting at base 1895 in SEQ ID NO. 1, and the capitalized bases indicate the seven repeated TAs. In each probe (3), the number of repeated TAs may be either 7 or 6. As described above, specific examples of the probe according to the present invention may be strands complementary to oligonucleotides indicated in the above table.

The aforementioned probes are examples and the present invention are not limited thereto. With respect to the probe for UGT1A1*6, a preferable probe among the probes (1) is oligonucleotide consisting of the base sequence of SEQ ID NO: 55 or oligonucleotide consisting of the base sequence of SEQ ID NO: 56. With respect to the probe for UGT1A1*27, a preferable probe among the probes (2) is oligonucleotide consisting of the base sequence of SEQ ID NO: 62 or oligonucleotide consisting of the base sequence of SEQ ID NO: 102. With respect to the probe for UGT1A1*28, a preferable probe among the probes (3) is oligonucleotide consisting of the base sequence of SEQ ID NO: 69.

When two or more of these probes are used, as described above, it is preferable that they be labeled with different fluorescent dyes (fluorescent dyes that are detected at different wavelengths). For instance, when the probes indicated in the above table are guanine quenching probes, it is preferable that in each probe for UGT1A1*6 and each probe for UGT1A1*27, cytosine at the 3' end thereof be labeled with a fluorescent dye (for instance, Pacific Blue or TAMRA) as described above and in each probe for UGT1A1*28, cytosine at the 5' end thereof be labeled with a fluorescent dye (for instance, BODIPY FL) as described above. Furthermore, a probe with the 5' end labeled with a fluorescent dye may have the 3' end, to which a phosphate group further may be added, in order to prevent the probe itself from elongating.

Next, with respect to the detection method of the present invention, a method of detecting three polymorphisms, UGT1A1*28, UGT1A1*6, and UGT1A1*27, in the UGT1A1 gene using the following probes is described as an example. However the present invention is not limited thereto.

<Probes>

Probe for UGT1A1*6
(SEQ ID NO: 55)
5'-agagacaGagcattttacac-(Pacific Blue)-3',
or (SEQ ID NO: 56)
5'-gagacaGagcattttacac-(Pacific Blue)-3'

Probe for UGT1A1*27
(SEQ ID NO: 62)
5'-ttattcccAgtatgcaacc-(TAMRA)-3',
or (SEQ ID NO: 102)
5'-gttgcatacTgggaataaac-(TAMRA)-3'

Probe for UGT1A1*28
(SEQ ID NO: 69)
5'-(BODIPY FL)-ccaTATATATATATATAtaagtaggagag-3'

First, using a reaction solution containing the aforementioned three labeled probes added thereto, PCR was performed as described above, and thereby the three regions of the UGT1A1 gene are amplified at the same time in the same reaction solution. The reaction solution contains, for example, a primer set for amplifying the UGT1A1 gene of the present invention, DNA polymerase, dNTP, a sample containing nucleic acid to serve as a template, and the aforementioned three probes. In addition to them, various additives that can be used for amplifying nucleic acid may be contained.

Next, the amplification products thus obtained are dissociated and then single-stranded DNA obtained through dissociation is hybridized with the labeled probes. This can be carried out through, for example, a change in the temperature of the reaction solution.

The heating temperature in the dissociation step is not particularly limited as long as it allows the amplification products to be dissociated. It is, for example, 85 to 95° C. The heating time also is not particularly limited and generally is 1 second to 10 minutes and preferably 1 second to 5 minutes.

The dissociated single-stranded DNAs can be hybridized with the labeled probes by, for example, decreasing the heating temperature employed in the dissociation step after the dissociation step. The temperature condition is, for example, 40 to 50° C.

The temperature of the reaction solution is changed and thereby signal values that indicate the melting states of hybridization products between the amplification products and the labeled probes are measured. Specifically, for example, the reaction solution (the hybridization products between the single-stranded DNAs and the labeled probes) is heated, and thereby the change in the signal values accompanying the temperature rise is measured. As described above, when, for example, a probe (guanine quenching probe), in which the base C at the end has been labeled, is used, fluorescence decreases (or quenches) in the state where the probe has been hybridized with the single-stranded DNA, while fluorescence is emitted in the state where the probe has been dissociated. Accordingly, for example, the hybridization product in which the fluorescence has decreased (or quenched) is heated gradually and the increase in fluorescence intensity accompanying the temperature rise may be measured.

The temperature range in which the change in fluorescence intensity is to be measured is not particularly limited. For example, the start temperature is room temperature to 85° C. and preferably 25 to 70° C., while the end temperature is, for example, 40 to 105° C. Furthermore, the rate of temperature rise is not particularly limited and is, for example, 0.1 to 20° C./sec and preferably 0.3 to 5° C./sec.

Next, the Tm value is determined by analyzing a change in the signal. Specifically, the amount of change in the fluorescence intensity per unit time at each temperature (−d fluorescence intensity increase/dt) is calculated from the fluorescence intensity obtained and the temperature at which the lowest value is obtained is determined as the Tm value. It is also possible to determine, as the Tm value, the point at which the amount of increase in the fluorescence intensity per unit time (fluorescence intensity increase/t) is the highest. On the contrary, the amount of decrease in the fluorescence intensity is measured when the labeled probe used is not a quenching probe but a probe that does not exhibit a signal independently but exhibits a signal after hybridization.

In the present invention, in order to detect three polymorphisms, UGT1A1*6, UGT1A1*27, and UGT1A1*28, the respective Tm values are determined under conditions according to the respective labels of the three probes. Pacific Blue, a probe for UGT1A1*6, can be detected with, for example, a detection wavelength of 450 to 480 nm, TAMRA, a probe for UGT1A1*27, with, for example, a detection wavelength of 585 to 700 nm, and BODIPY FL, a probe for UGT1A1*28, with, for example, a detection wavelength of 515 to 555 nm.

From such Tm values, the genotypes in the respective sites to be detected are determined. In the Tm analysis, the case of a perfectly complementary hybrid (match) results in a higher Tm value indicating dissociation than that obtained in the case of a hybrid including a different single base (mismatch). Accordingly, when with respect to the probe, the Tm value obtained in the case of a perfectly complementary hybrid and the Tm value obtained in the case of a hybrid including a different single base are determined beforehand, the genotype at each site to be detected can be determined. For example, in the case where the base located at the site to be detected is assumed to be of a mutation type (with, for instance, A at base 2160 in SEQ ID NO: 1), when using a probe complementary to the sequence to be detected containing the base, the polymorphism of the amplification product can be judged as a mutation type if the Tm value of the resultant hybrid is equal to the Tm value of a perfectly complementary hybrid. Furthermore, the polymorphism of the amplification product can be judged as a wildtype (with, for example, G at base 2160 in SEQ ID NO: 1) if the Tm value of the resultant hybrid is equal to the Tm value of the hybrid including a different single base (i.e. a lower value than the Tm value of the perfectly complementary hybrid). Moreover, when both the Tm values are detected, it can be judged as heterozygote. Thus, the genotypes of the polymorphisms, UGT1A1*6, UGT1A1*27, and UGT1A1*28, can be judged from the three Tm values with respect to the respective labeled probes.

In the present invention, for example, a change in the signal during hybridization may be measured instead by the method in which the temperature of a reaction solution containing the probes is increased (a hybridization product is heated) and a change in the signal accompanying the temperature rise is measured as described above. In other words, when the temperature of the reaction solution containing the aforementioned probes is decreased to form hybridization products, the change in the signal accompanying the temperature decrease may be measured.

Specifically, when using a labeled probe that exhibits a signal independently but does not exhibit a signal after hybridization (for example, a guanine quenching probe), the labeled probe emits fluorescence in the state where single-stranded DNA and the probe are dissociated, but the fluorescence decreases (or quenches) when a hybrid is formed through temperature decrease. Accordingly, for example, the temperature of the reaction solution is decreased gradually and the decrease in fluorescence intensity accompanying the temperature decrease may be measured. On the other hand, when using a labeled probe that does not exhibit a signal independently but exhibits a signal after hybridization, the labeled probe does not emit fluorescence in the state where single-stranded DNA and the probe are dissociated, but the fluorescence is emitted when a hybrid is formed through temperature decrease. Accordingly, for example, the temperature of the reaction solution is decreased gradually and thereby the increase in fluorescence intensity accompanying the temperature decrease may be measured.

When one or two of the three types of polymorphisms (UGT1A1*28, UGT1A1*6, and UGT1A1*27) in the UGT1A1 gene are to be analyzed, for instance, a primer set for amplifying the UGT1A1 gene of the present invention may be used that includes one or two types of primer sets corresponding to the target regions that are selected from the primer sets (1) to (3), and furthermore, one or two probes that hybridize to target sites to be detected may be used.

Next, examples of the present invention are described. However, the present invention is not limited by the following examples.

Example 1

Blood was collected from nine subjects using heparin lithium blood collection tubes (Samples 1 to 9). Subsequently, 10 µL of blood thus obtained and 90 µL of distilled water were mixed together. Further, 10 µL of this mixture and 90 µL of distilled water were mixed together. Thereafter, 10 µL of the mixture was added to 40 µL of PCR reaction solution having the following composition, and then PCR was performed using a thermal cycler. Conditions for PCR were as follows. That is, after treating at 95° C. for 60 seconds, one cycle of treatment at 95° C. for 1 second and at 54° C. for 10 seconds was repeated for 50 cycles, and further it was treated at 95° C. for 1 second and at 40° C. for 60 seconds. Subsequently, the PCR reaction solution was heated from 40° C. to 95° C. at a rate of temperature rise of 1° C./3 seconds, and the change in fluorescence intensity over time was measured. The measurement wavelength was 450 to 480 nm (for detection of the fluorescent dye, Pacific Blue), 515 to 555 nm (for detection of the fluorescent dye, BODIPY FL), and 585 to 700 nm (for detection of the fluorescent dye, TAMRA). The time required for 50 cycles of PCR was approximately one hour.

TABLE 6

| <PCR reaction solution; unit: μl> | |
|---|---|
| Distilled water | 19.875 |
| 5% NaN$_3$ | 0.5 |
| 20% BSA | 1 |
| 40% Glycerol | 3.125 |
| 10× Gene Taq buffer* | 5 |
| 2.5 mM dNTPs | 4 |
| 100 mM MgCl$_2$ | 1 |
| 5 μM probe for UGT1A1*6 | 1 |
| 5 μM probe 1 for UGT1A1*27 | 0.5 |
| 5 μM probe 2 for UGT1A1*27 | 1 |
| 5 μM probe for UGT1A1*28 | 0.5 |
| 100 μM UGT1A1*6 F1 primer | 0.25 |
| 100 μM UGT1A1*6 R1 primer | 0.5 |
| 100 μM UGT1A1*27 F2 primer | 0.25 |
| 100 μM UGT1A1*27 R2 primer | 0.5 |
| 100 μM UGT1A1*28 F3 primer | 0.25 |
| 100 μM UGT1A1*28 R3 primer | 0.5 |
| 5 U/μl Gene Taq FP* | 0.25 |
| Total | 40 μL |

*Trade name, Gene Taq Fp: manufactured by Nippon Gene Co., Ltd.

<Probes>

```
Probe for UGT1A1*6
                                     (SEQ ID NO: 55)
5'-agagacagagcattttacac-(Pacific Blue)-3'

Probe 1 for UGT1A1*27
                                     (SEQ ID NO: 62)
5'-ttattcccagtatgcaacc-(TAMRA)-3'

Probe 2 for UGT1A1*27
                                     (SEQ ID NO: 62)
5'-ttattcccagtatgcaacc-P-3'

Probe for UGT1A1*28
                                     (SEQ ID NO: 69)
5'-(BODIPY FL)-ccatatatatatatataagtaggagag-P-3'
```

<Primer Set>

```
UGT1A1*6 F1 primer
5'-agcagaggggacatgaaata-3'    (SEQ ID NO: 4)

UGT1A1*6 R1 primer
5'-aacattatgcccgagactaac-3'   (SEQ ID NO: 13)

UGT1A1*27 F2 primer
5'-agaactttctgtgcgacg-3'      (SEQ ID NO: 21)

UGT1A1*27 R2 primer
5'-cagatgcagagctcaatagg-3'    (SEQ ID NO: 29)

UGT1A1*28 F3 primer
5'-gtcacgtgacacagtcaaac-3'    (SEQ ID NO: 42)

UGT1A1*28 R3 primer
5'-cctttgctcctgccagag-3'      (SEQ ID NO: 48)
```

The Tm value of a hybrid that matches with the probe for UGT1A1*6 is 63° C. and that of a hybrid that mismatches therewith is 56° C., the Tm value of a hybrid that matches with the probe for UGT1A1*27 is 61° C. and that of a hybrid that mismatches therewith is 56° C., and the Tm value of a hybrid that matches with the probe for UGT1A1*28 is 58° C. and that of a hybrid that mismatches therewith is 54° C.

Figure 2:
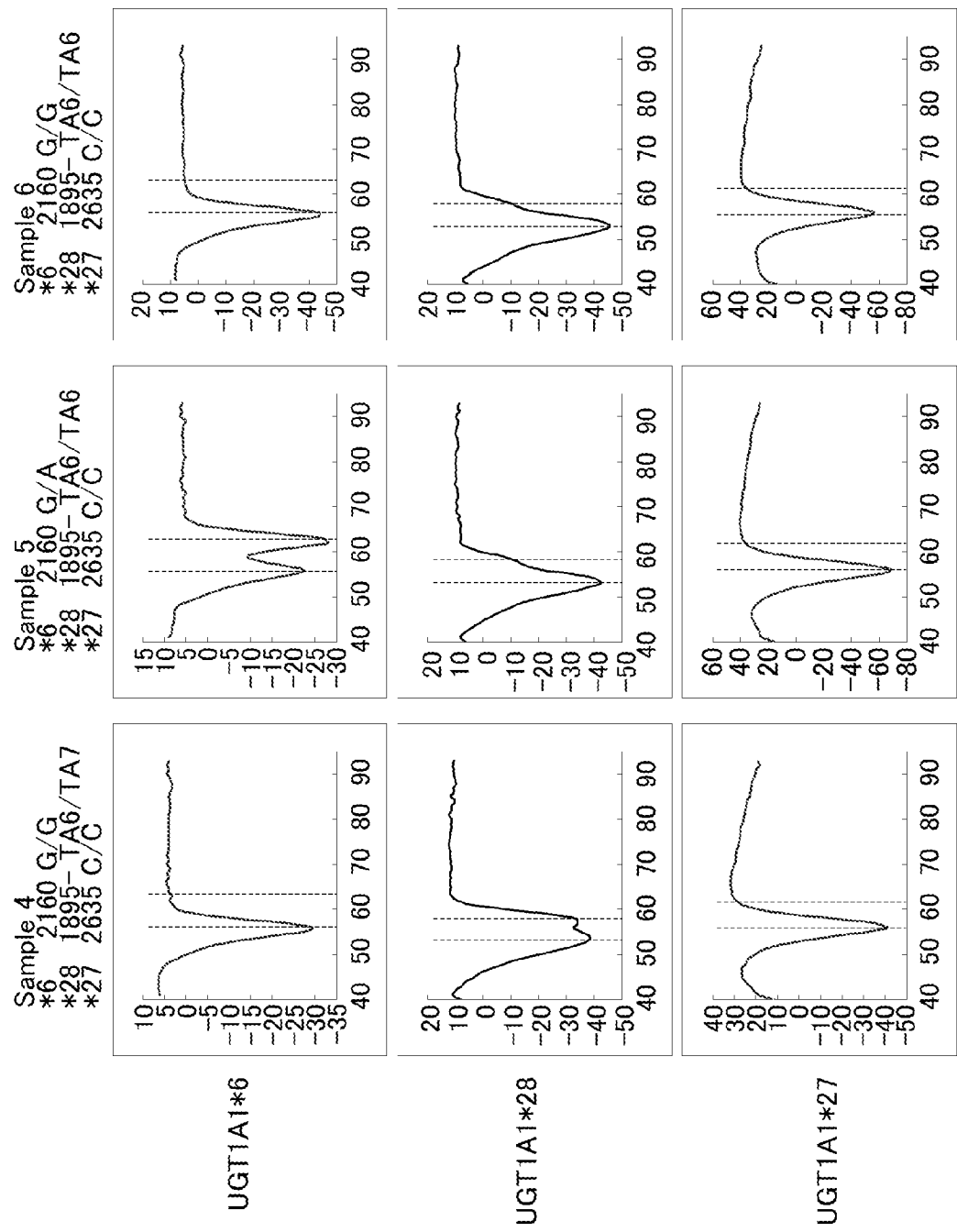
FIG. 2 shows graphs indicating the results of Tm analysis in Example 1 of the present invention described above.
Figure 3:
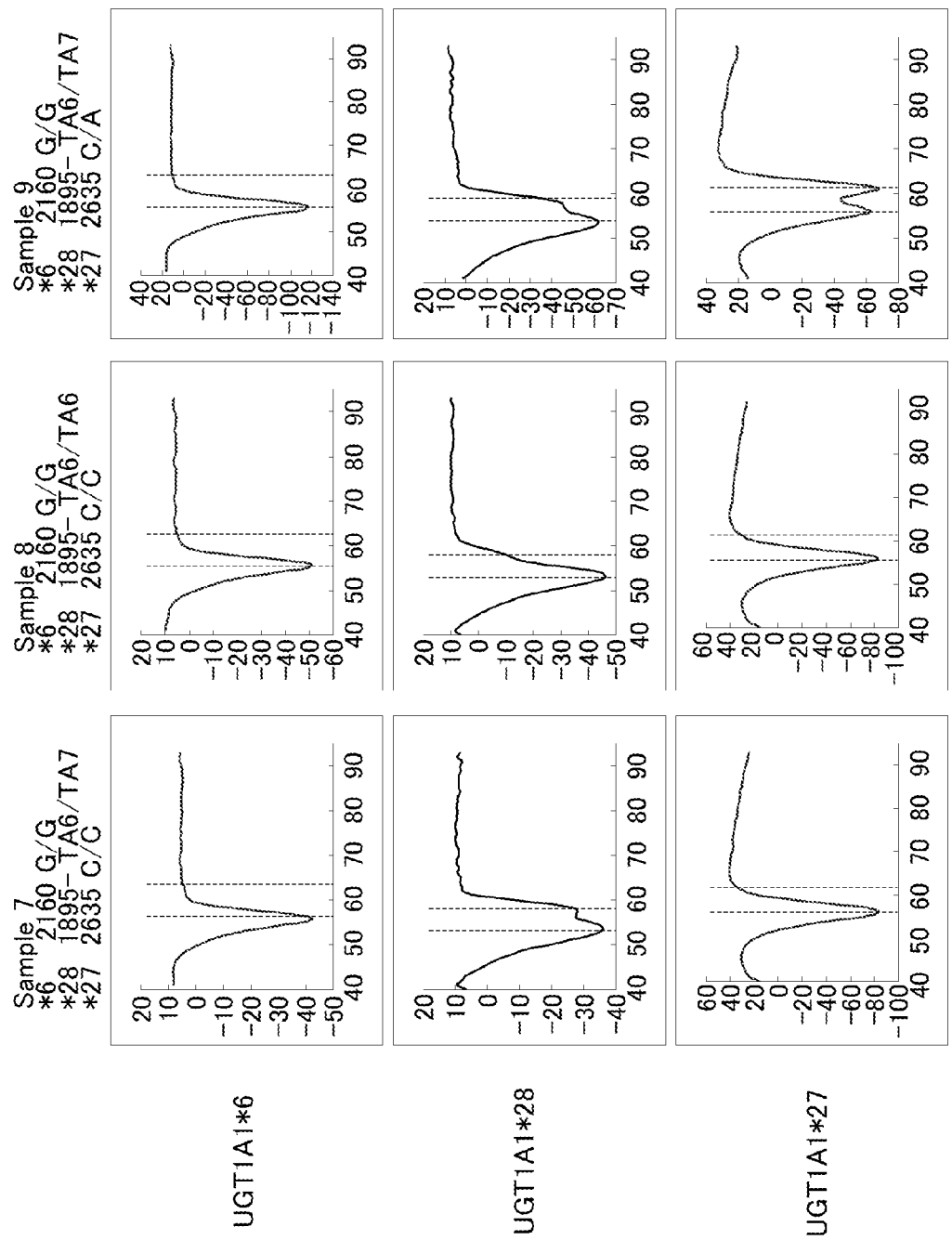
FIG. 3 shows graphs indicating the results of Tm analysis in Example 1 of the present invention described above.

The results for Samples 1 to 9 are indicated in FIGS. 1 to 3. These figures show graphs of Tm analysis that indicate the changes in fluorescence intensity accompanying temperature rise. The differential value of the vertical axis indicates "−d fluorescence intensity increase/dt", while the horizontal axis indicates temperature (the same applies below). As shown in these graphs, the genotypes of UGT1A1*6, UGT1A1*27, and UGT1A1*28 in each sample were determined from the peaks of the signals. In order to support the results of these examples, with respect to nine subjects, the genotypes of UGT1A1*6, UGT1A1*27, and UGT1A1*28 were confirmed by the RFLP method and the sequencing method. As a result, the same results as those obtained in the example were obtained. Accordingly, the use of a primer set of the present invention made it possible to amplify three regions of the UGT1A1 gene simultaneously in the same reaction solution using a whole blood sample that had not been pretreated and to analyze the three types of polymorphisms using the same reaction solution.

Example 2

Blood was collected from two subjects using EDTA blood collection tubes (Samples 1 and 2). Subsequently, 10 μL of blood thus obtained and 70 μL of diluent A described below were mixed together. Further, 10 μL of this mixture and 70 μL of diluent B described below were mixed together Subsequently, 10 μL of the mixture thus obtained was heat-treated at 95° C. for five minutes. Thereafter, this was added to 46 μL of PCR reaction solution having the following composition, and then PCR was performed using a thermal cycler. Conditions for PCR were as follows. That is, after treating at 95° C. for 60 seconds, one cycle of treatment at 95° C. for 1 second and at 60° C. for 15 seconds was repeated for 50 cycles, and further it was treated at 95° C. for 1 second and at 40° C. for 60 seconds. Subsequently, the PCR reaction solution was heated from 40° C. to 75° C. at a rate of temperature rise of 1° C./3 seconds, and the change in fluorescence intensity over time was measured. The measurement wavelength was 450 to 480 nm (for detection of the fluorescent dye, Pacific Blue), 515 to 555 nm (for detection of the fluorescent dye, BODIPY FL), and 585 to 700 nm (for detection of the fluorescent dye, TAMRA).

<Diluent A>
10 mM Tris-HCl (pH 8), 0.1 mM EDTA, 0.05% NaN$_3$, 0.3% SDS

<Diluent B>
10 mM Tris-HCl (pH 8), 0.1 mM EDTA, 0.05% NaN$_3$

TABLE 7

| <PCR reaction solution; unit: μl> | |
|---|---|
| Distilled water | 15 |
| 5% NaN$_3$ | 0.5 |
| 20% BSA | 0.5 |
| 40% Glycerol | 12.5 |
| 10× Gene Taq buffer* | 5 |
| 2.5 mM dNTPs | 4 |
| 5 μM probe for UGT1A1*6 | 2 |
| 5 μM probe for UGT1A1*27 | 2 |

TABLE 7-continued

<PCR reaction solution; unit: μl>

| | |
|---|---|
| 5 μM probe for UGT1A1*28 | 2 |
| 100 μM UGT1A1*6 F1 primer | 0.25 |
| 100 μM UGT1A1*6 R1 primer | 0.5 |
| 100 μM UGT1A1*27 F2 primer | 0.5 |
| 100 μM UGT1A1*27 R2 primer | 0.25 |
| 100 μM UGT1A1*28 F3 primer | 0.25 |
| 100 μM UGT1A1*28 R3 primer | 0.5 |
| 5 U/μl Gene Taq FP* | 0.25 |
| Total | 46 μL |

*Trade name, Gene Taq Fp: manufactured by Nippon Gene Co., Ltd.

<Probes>

```
Probe for UGT1A1*6
                                     (SEQ ID NO: 56)
5'-gagacagagcattttacac-(Pacific Blue)-3'

Probe for UGT1A1*27
                                     (SEQ ID NO: 102)
5'-gttgcatacTgggaataaac-(TAMRA)-3'

Probe for UGT1A1*28
                                     (SEQ ID NO: 69)
5'-(BODIPY FL)-ccatatatatatatataagtaggagag-P-3'
```

<Primer Set>

```
    UGT1A1*6 F1 primer
                                     (SEQ ID NO: 81)
    5'-tgaaatagttgtcctagcacctgacg-3'

UGT1A1*6 R1 primer
                                     (SEQ ID NO: 91)
    5'-caaaagactctttcacatcctccctttgg-3'

UGT1A1*27 F2 primer
                                     (SEQ ID NO: 92)
    5'-ccttttcacagaactttctgtgcgacg-3'

UGT1A1*27 R2 primer
                                     (SEQ ID NO: 98)
    5'-gccagacagatgcagagctcaatagg-3'

UGT1A1*28 F3 primer
                                     (SEQ ID NO: 123)
    5'-agcttttttatagtcacgtgacacagtcaaac-3'

UGT1A1*28 R3 primer
                                     (SEQ ID NO: 46)
    5'-cgcctttgctcctgccagag-3'
```

The Tm value of a hybrid that matches with the probe for UGT1A1*6 is 57° C. and that of a hybrid that mismatches therewith is 50° C., the Tm value of a hybrid that matches with the probe for UGT1A1*27 is 57° C. and that of a hybrid that mismatches therewith is 50° C., and the Tm value of a hybrid that matches with the probe for UGT1A1*28 is 53° C. and that of a hybrid that mismatches therewith is 49° C.

Figure 4:
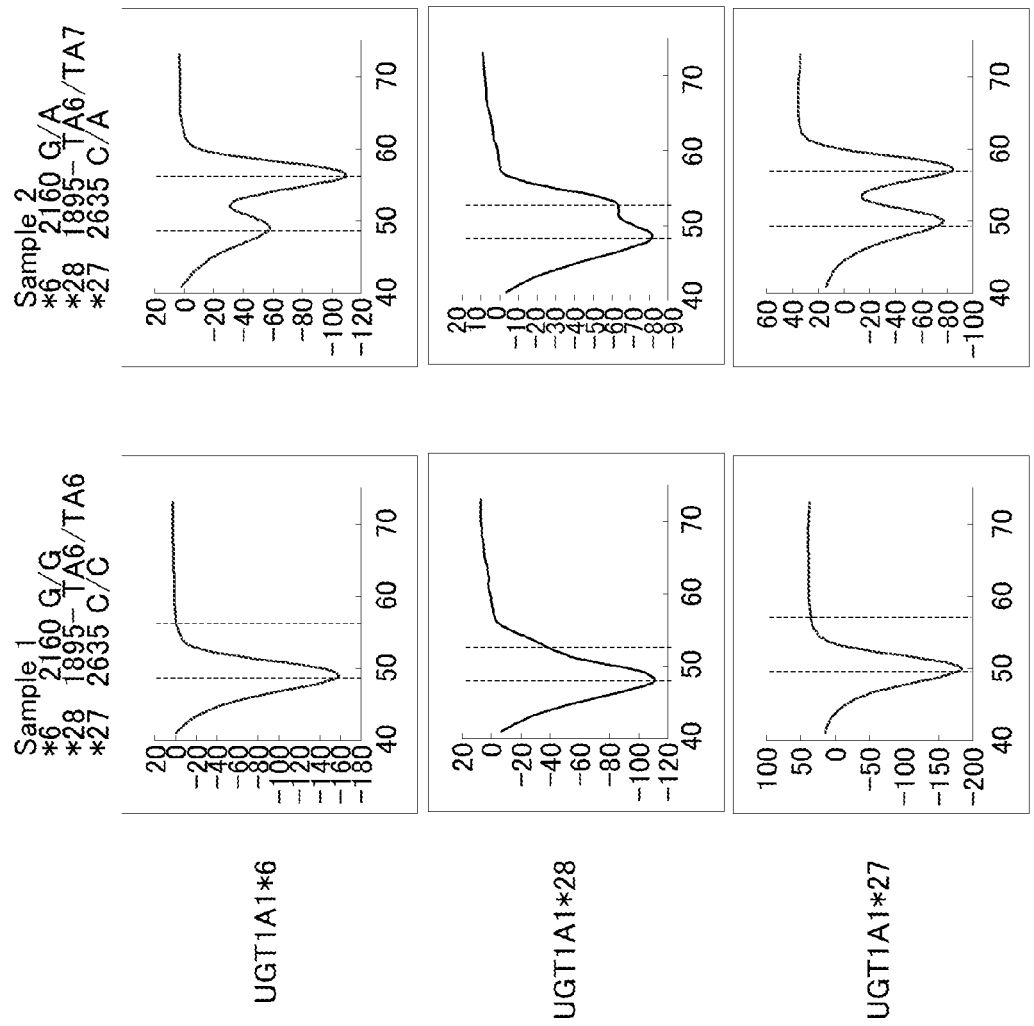
FIG. 4 shows graphs indicating the results of Tm analysis in Example 2 of the present invention.

Results of Samples 1 and 2 are indicated in FIG. 4. FIG. 4 shows graphs of Tm analysis that indicate the changes in fluorescence intensity accompanying temperature rise. The differential value of the vertical axis indicates "−d fluorescence intensity increase/dt", while the horizontal axis indicates temperature. As shown in these graphs, the genotypes of UGT1A1*6, UGT1A1*27, and UGT1A1*28 in each sample were determined from the peaks of the signals. In order to support the results of these examples, with respect to two subjects, the genotypes of UGT1A1*6, UGT1A1*27, and UGT1A1*28 were confirmed by the RFLP method and the sequencing method. As a result, the same results as those obtained in the example were obtained. Accordingly, the use of a primer set of the present invention made it possible to amplify three regions of the UGT1A1 gene a simultaneously in the same reaction solution using a whole blood sample that had not been pretreated and to analyze the three types of polymorphisms using the same reaction solution.

INDUSTRIAL APPLICABILITY

As described above, the primer set of the present invention makes it possible to amplify specifically and efficiently a region including a site where a particular polymorphism (UGT1A1*28. UGT1A1*6, or UGT1A1*27) is generated in the UGT1A1 gene. This allows time and cost to be reduced, which is different from the conventional methods as described above. Furthermore, as described above, since the region including a site to be detected of a polymorphism is amplified specifically, for example, the use of a probe complementary to a sequence to be detected including the site to be detected makes it possible to perform Tm analysis directly using the aforementioned reaction solution to type the polymorphism. Moreover, since amplification and typing can be carried out using one reaction solution, the operation can be automated. The use of the primer set of the present invention allows a pretreatment to be omitted even in the case of, for example, a contaminated sample (for instance, whole blood or oral mucosa), and therefore the amplification reaction can be carried out quicker and more easily. Furthermore, when the primer set of the present invention is used, the amplification reaction can be carried out with higher amplification efficiency as compared to conventional cases and thus the reaction time can also be shortened. According to the primer set of the present invention, the reagent including the same, as well as the method of manufacturing an amplification product using them, since the polymorphism in the UGT1A1 gene can be analyzed quickly and simply, it can be said that they are considerably effective in the field of medicine.

[Sequence Table] TF07037-01.5T25.txt

---

The invention claimed is:

1. A reagent composition comprising (i) a primer set including a first oligonucleotide consisting of SEQ ID NO: 123 and a second oligonucleotide consisting of SEQ ID NO: 46, and (ii) a probe consisting of a base sequence of SEQ ID NO: 69.

2. The reagent composition according to claim 1, wherein the probe is a fluorescently-labeled probe.

3. A polymorphism analysis method of analyzing a polymorphism of a site to be detected in the UGT1A1 gene, wherein the method comprises the following processes (i) to (iv):
   (i) amplifying a region including a site to be detected in the UGT1A1 gene in a reaction solution comprising the reagent composition of claim 1,
   (ii) preparing a reaction solution that contains the amplification product obtained in process (1) and a probe capable of hybridizing to the site to be detected,
   (iii) measuring signal values that indicate molten states of a hybridization product between the amplification product and the probe while changing the temperature of the reaction solution, and
   (iv) determining a polymorphism of the site to be detected from a change in the signal values accompanying a change in the temperature.

4. The method of claim 3, wherein the probe is a fluorescently-labeled probe.

5. The method of claim 3, wherein the sample is a biological sample.

6. The method of claim 3, wherein the biological sample is whole blood.

7. The method of claim 3, wherein the ratio of the whole blood sample to be added to the reaction solution is 0.1 to 0.5 vol %.

8. The polymorphism analysis method according to claim 3, wherein in the process (i), a probe that can hybridize to the site to be detected is added to the reaction solution prior to an amplification reaction.

9. The reagent composition according to claim 1, further comprising one of the following primer sets (1) and (2):
   Primer set (1):
      a primer set of a pair of primers including a forward primer consisting of the following oligonucleotide (F1) and a reverse primer consisting of the following oligonucleotide (R1):
   (F1): oligonucleotide consisting of a sequence selected from a group consisting of SEQ ID NO: 2 to 6 and SEQ ID NO: 74 to 90, and
   (R1): oligonucleotide consisting of a sequence selected from a group consisting of SEQ ID NO: 7 to 17, SEQ ID NO: 91, and SEQ ID NO: 106 to 122, and
   Primer set (2):
      a primer set of a pair of primers including a forward primer consisting of the following oligonucleotide (F2) and a reverse primer consisting of the following oligonucleotide (R2):
   (F2): oligonucleotide consisting of a sequence selected from a group consisting of SEQ ID NO: 18 to 24 and SEQ ID NO: 92 to 97, and
   (R2): oligonucleotide consisting of a sequence selected from a group consisting of SEQ ID NO: 25 to 32 and SEQ ID NO: 98 to 99.

10. The reagent composition according to claim 9, wherein the primers have melting temperatures (Tm) between 48-60° C.

11. The reagent composition according to claim 9, wherein the primers for primer set (1) have melting temperature between 46-66 ° C., and the primers for primer set (2) have melting temperature between 47-61° C.

12. The reagent composition according to claim 9, wherein the primer sets (1) and (2) are the following primer sets (1') and (2'), respectively:
   Primer set (1'):
      a primer set of a pair of primers including a forward primer consisting of the following oligonucleotide (F1') and a reverse primer consisting of the following oligonucleotide (R1'):
   (F1'): at least one oligonucleotide selected from oligonucleotide consisting of the sequence of SEQ ID NO: 4 and oligonucleotide consisting of the sequence of SEQ ID NO: 81, and
   (R1'): at least one oligonucleotide selected from oligonucleotide consisting of the sequence of SEQ ID NO: 13 and oligonucleotide consisting of the sequence of SEQ ID NO: 91, and
   Primer set (2'):
      a primer set of a pair of primers including a forward primer consisting of the following oligonucleotide (F2') and a reverse primer consisting of the following oligonucleotide (R2'):
   (F2'): at least one oligonucleotide selected from oligonucleotide consisting of the sequence of SEQ ID NO: 21 and oligonucleotide consisting of the sequence of SEQ ID NO: 92, and
   (R2'): at least one oligonucleotide selected from oligonucleotide consisting of the sequence of SEQ ID NO: 29 and oligonucleotide consisting of the sequence of SEQ ID NO: 98.

* * * * *

SEQUENCE LISTING

<160> NUMBER OF SEQ ID NOS: 124

<210> SEQ ID NO 1
<211> LENGTH: 16944
<212> TYPE: DNA
<213> ORGANISM: Homo sapiens

<400> SEQUENCE: 1
tgcatgatgc aggaaagtca taaaatcatt acagtggtga cttatgtgtt tatagcccct      60
ttactgtcta taatctgcaa atgaactcac acagcattgg gactttggaa gaattatcac     120

```
ccttaaggtt taaattaaac tgtgaatttc agaatttcta ataaggacac aacaaagagt    180
gaaagcattg ctatgtctat tctgcttgcc cagaatcttg gtcctaaaaa atgaagagtg    240
tttgggtgtg gggaggagct tcagtgtgca tgtgcatgca aagtacctac tctaaggaga    300
agaatgagag ggtaccctaa ttacctgtta atatgtccca taggacacca aaactctagt    360
tagctgtttc tctatgatcc tctaagcaca tccccaagta tggctggcca gtgatgtgta    420
tggttcaaat gttgggatct gtgcagttat cttggaattg tatagtacag cagtatatcc    480
cccccaaaaa gagtgtaata cttccaattc tggctgcaca atacttgccc catagtccat    540
ggtcaataaa tacaaatttg agttgttttt gctcatcttt ccctttttgac ttcaactcag    600
tcatcagaat ttccccaaat gcctttcccc tggatcttgg gccagtggaa tgagtacaat    660
ttaacttaat tgaatttgct tatctatttg gtttcctgtt gtgaacaaaa gttctctgaa    720
aaggaatttg gaagaaagag actttgttct agtgaacagt ttgcaaacca gggagttaca    780
gcctctggta cgcaatgaag gtgagttcca cagaacacaa ggcaggcagg tttcacggca    840
aaaagttcct tcccaggttc ccaatcaggt ccatttatgc aaatgaagga tggaaacttg    900
cttagttctt attggtcact gcagctgcat tctgattggt tgatgaagct gagccctgag    960
tggctgaggt gggtgagctt taattggttg gttcaggtga gcgctgaaaa tctcaactat   1020
aaaaaggtac aggttttcag gatactcaga gtaaccgtgt gacctgtagt aagcaaaggg   1080
ccagttggct ctattttaaa tccaggccca gttagccact caagatctat cttacaggac   1140
tggctctttc aggttcacac taataaaggc ctgtccttgg ggaagacttc tgttcacatg   1200
cgctccagtg aatttcccTt tctggtcatt ctctacccca gcacgccccc cacccccgcc   1260
ccgcccacc cacccacctg ttcatttcct tcttagcatg cttcacgatt tctaagttcc   1320
tgctcatgtg tttaaattgt gagtctggct cacctcatgg cgcgtgctcg tgtggtgggc   1380
tctgctgcag cctcaagacc ccacactgtg ctggactcaa taaatattgt tggacgaagg   1440
aatgaaacac atgatacaag tgagcaggca gtaccggggg agctgtggag tgggcactct   1500
tacaggtttc catggcgaaa gcgggggtac agttgtgttc ttttctttct aaaaggcttt   1560
ctaaaaagcc ttctgtttaa tttctggaaa agaagcctaa cttgttcact acatagtcgt   1620
ccttcttcct ctctggtaac acttgttggt ctgtggaaat actaatttaa tggatcctga   1680
ggttctggaa gtactttgct gtgttcactc aagaatgtga tttgagtatg aaattccagc   1740
cagttcaact gttgttgcct attaagaaac ctaataaagc tccaccttct ttatctctga   1800
aagtgaactc cctgctacct ttgtggactg acagctttt atagtcacgt gacacagtca   1860
aacattaact tggtgtatcg attggttttt gccatatata tatatatata agtaggagag   1920
ggcgaacctc tggcaggagc aaaggcgcca tggctgtgga gtcccagggc ggacgcccac   1980
ttgtcctggg cctgctgctg tgtgtgctgg gcccagtggt gtcccatgct gggaagatac   2040
tgttgatccc agtggatggc agccactggc tgagcatgct tggggccatc cagcagctgc   2100
agcagagggg acatgaaata gttgtcctag cacctgacgc ctcgttgtac atcgagacg   2160
gagcatttta caccttgaag acgtaccctg tgccattcca aagggaggat gtgaaagagt   2220
cttttgttag tctcgggcat aatgttttg agaatgattc tttcctgcag cgtgtgatca   2280
aaacatacaa gaaaataaaa aaggactctg ctatgctttt gtctggctgt tcccacttac   2340
tgcacaacaa ggagctcatg gcctccctgg cagaaagcag ctttgatgtc atgctgacgg   2400
acccttcct tccttgcagc cccatcgtgg cccagtacct gtctctgccc actgtattct   2460
tcttgcatgc actgccatgc agcctggaat ttgaggctac ccagtgcccc aacccattct   2520
```

-continued

```
cctacgtgcc caggcctctc tcctctcatt cagatcacat gaccttcctg cagcgggtga    2580
agaacatgct cattgccttt tcacagaact ttctgtgcga cgtggtttat tccccgtatg    2640
caacccttgc ctcagaattc cttcagagag aggtgactgt ccaggaccta ttgagctctg    2700
catctgtctg gctgtttaga agtgactttg tgaaggatta ccctaggccc atcatgccca    2760
atatggtttt tgttggtgga atcaactgcc ttcaccaaaa tccactatcc caggtgtgta    2820
ttggagtggg acttttacat gcgtatattc tttcagatgt attactttgg atcgattaac    2880
tagccccaga tatatgctga gcaagcattc tgagataatt taaaatgccc tcttttgtta    2940 attttgact cctaggtttg agtctgtctt tggcatcatc ttctggatga tttcttggta    3000
tctgagattt cgggaaagca ttccttggac attttactct gtgtgctcca gtggatagta    3060
atcaattaga acaacaagc tgttaaatgc cataggcaca gaatgctggg tttggggcac    3120
cctgcagaaa actcagttga agcctgcacc ttgccctgga ttcagtcagg caggcaatgt    3180
tcaggactga tgaaatcatt cttttgatgat gatagatcct ggaaatgaaa gttgcctttg    3240
tgaccctggt taaagctcca gtttctaaat attctgataa gaagctaaat cctgcagtcc    3300
gttctcttct aatgagtgaa tcaccagaca gtcaggttct gacatgatac agaaaggttg    3360
taggtttcat tctcaagcta ttaggtttat ttttccccta cagagtttga agtatgcaaa    3420
aagtagcatt cacatcctca tcgaaatctc agcagaggat agaaaagaac aggagaggct    3480
ccttcagatg gagcgttagg gaattactct ttgaggaggt gacatttcag agagcgttca    3540
ttcacttatc ctgcaaagat tggctgagga tctactggca gcccaggcac ttcccaggtg    3600
ctgcgtctgg ctcccattaa ggggactgat atcaccttcg gaggtgacct tatttccact    3660
atacctccaa tgtgatttgt atttttatttt tttttaatttt ctgtgcattt tccttcatag    3720
cacatcaaat atggcagcca tttcacttag atagttgttg attgtccgct tcacatcatg    3780
agccatgtgg ggaacctgtgt gactttgcat taatcacatc cactgtatgc ggcgtcctca    3840
acacctgcca atgggtctgc atgtatttgg cgccccataa atctcagcac ctaaggcaca    3900
gaataggcac ccaccgaata tgtgttacat taatgaatga gaagaaaggt gccaaccgag    3960
gtctagttaa tgggtcgaga gtaatccaca atagctcttt ttagttcttt gtactccagc    4020
tattacatac caatatgtat atagaaacat atgtaaaatt ttttggttgc tttttctaca    4080
aaatagagta acagtgtatt cccactgccc acttaccgat aatgtcatgg atatcactcc    4140
agttttaaat gctattactt tttaaactat gaaatagtat ttcatggtac ttgtgtacca    4200
cagtgtattc tgctggagat ctagtctagt tccccacaga ggaacattac aatttgtatt    4260
ccaggagttt tgttgttgtg acctcaaaca cttcctttaa aaagataagc tattttgtag    4320
tttaaaaaac atttgttctg tttctttctc attcatcttt tcttaagtat tttacacggt    4380
tttttttttt tggtcactac tgtgaatgtg ttatttttttt gcatttctat ctctagctga    4440
ttatctactc attactcagc tatctcatca aaatattgat tttcataata aaaaataata    4500
ggcagtcatt tgctgataaa gaaattttgg tttcttctct tataaattcc atgccaaata    4560
tcagggctat tgaatttatt agaatctcta aaaacagttg ataattctg gcaataggaa    4620 agatgcccgt cttgctgcta ttttagtgga aattgattat catttcatta ttttgcatta    4680
tgttagccat tgttttctga acaggcttta ttgatttaga taatttcctt ctttgcgtga    4740
ggatgtttgt aggagaggca ccgaacttta tcagctgcct ttctggcatt tattgatata    4800
accataaaag tctaagtggt gaactgtgtt gactacatat ttgttgttgc cttgtttggt    4860
gcagtcaggc ttaggtgtga aaatatgttt ttaaattgta ccttttagta acctgttttg    4920
```

```
tcttgttgca tgttttaatc tgaaattcca cttttttggat attaatatta ccacttctgt   4980 attattttg tttacatttc cctagcacat ctttagtact cctttgtctt caagctttct    5040 tccttttaa acaacatggc actggtattt ttaatccagt caggcagttg ctttaataag    5100
tgcattttgc ctatttgaat ctaacaatta atagatttga ttgtaactct ctcagtttac   5160
tttatgttta gttgactttg ccattctcct ttttccggat ttctactggt tggtcaagtt   5220
actgttctta ttttctcttt cttcctttgt taactaaaaa tgccactctg cactaccatt   5280
cctcttgtgt tgatggtcct attctcaata ctcttgataa aactcctgaa ctttaagaat   5340
aaagataaaa cttttattgc acaagaagt ccatagagaa agcacaacct ggcattggcg     5400
tgtctttggt gtgtctgaag gaaaagagat agtggaacaa cattgggaga aaggaatga    5460 aactcaagaa ttccaagatg ttcctcccct gccagggtaa gatagcagtg gttcacagac   5520
aatcgcaatg ctgggtctga gaaaaataac taaacagaag attagtgagg accaaggctt   5580
cgagatggcc aggagaggaa agcttgggag cagggaaggt tgagatatat gtgggttact   5640
gggaatgcgt gatggtgaag tcacagatga cccacatggt gtctaagtgc taagaagaa    5700 ttctgggaaa atgaaatgca tttgggaagg gaaaatctaa ttaaaagcct aaactaaaaa   5760
tacaaaattc ttggtaaagt ttaggagtta tgttaaatgt ctcattttgg ctggtgaagt   5820
ctcatcagaa cagggaaatt ctctcattca ggggcatctc atcttttctt tgaagggaat   5880
caatggtggg ggattggagt gttattttca gttaatatgt tgcttcactc tttggtcatt   5940
ccggtaactg tgaagtcagg gtgaagttta agggaagctt tgccaagtag gggatggact   6000
tcacctttat tgagcctcat agtagctggc tcaggtagga gttggccgtg atgacaactt   6060
ctctgcagtt tgccctgcgt gaatctccag atgaactttt gtgccattta aactttcgtg   6120
atctcctgct atttaacttc gaatgtttat ggacctgtgg gttcaatttt gtgtgaatca   6180
catcctgctg attgctgagt gggcgtgtgg gaggtgtgc ctggaggaga acttagactc     6240 ggcctttttcc agatgagctt cagtgtaaga gtgggtttca tgaagagcaa aggtcctagg   6300
aaatttaagt aagccattta ccaacgctca gaagaaagaa cttgaagagc acttggaaat   6360
gagctgtgtc tccccaagaa agagggagag aaagagggga gagatgtggt gcagacccta   6420
gggaggaagg agttcagaaa aaccatcctc agggtgttct tgctacaaac caaaaaatgc   6480
agcatggtgg tggggaggat gactctgtcc tccctgactt ttagatgagc caagggaaa     6540 aggcaaagac aaagccctta agagccagag gactcacgag ggcctggggc tggtgagagt   6600
ggcggggaga gagggctcac cttgggagaa ggatggtcag tgtctggggc tttcctggtc   6660
atgttccaaa tcaggcttgg caggagtcct gctgtgcaaa ttgcgtttgc tgagccctgt   6720
cagaggtctc ctgtgtctca catctagggt gaccagcatc ctggcttcct caggactgtt   6780
caggttttag cactgaacat cacatgtcct agggaacccc tcagtttggg caagccctgc   6840
cacatcacac aatcatatta gtgccctcag tattctttgc aaacataaaa ccatagactc   6900
agtaatccca ttactgggta tatcccaaa gaaatataaa ttattctact ataaagacac     6960
atgcacatat ttgtttattg cagcactatt cacaataaca aagtcatgga accaacccag   7020
atgcccatca atggtagatt ggataaagaa aatgtggtac atatacacca tggaatacta   7080
tgcagccata acaaggaatg agatcatatt ctttgcaagg acatggatga agctggaagc   7140
catcatcctc cacaaactaa cacaggaaca gaaaatcaaa caccgcatgt tctcactcat   7200
aagtgggagt tgaacagtga gaatgcgtag acgcagggag gggaacaaca cacaccaggg   7260
cttgtggcgg ggtgaggggt gaggggagga acttagagga taggtcaata ggtgcagcaa   7320
```

-continued

```
accaccatgg catatgtatc ccagaacttc aagtaaataa taataataat aattaataat   7380
aataataata ataaataaac ccataaagcc atttgagaga ttcttggggg attcattgga   7440
ccactgaaaa tctacagtga gaaagaatt gccatgttga tgaaacagga aaactttcct   7500
tgtccccctc acagagcatg tgacagcggg aggggctcac tttctcagtg cgccactgct   7560
caaacctcta ggggagcata cagacgggca ggttgtgggg ctctgacctc accggcagtg   7620
tctagaggtg gatgtttaca gctcctgaag ctccagtggg cgtgggttat ggccttcttt   7680
tagttttgcc ctctatagtc agcttgtgtt aaccagctca attacaccct ctaccttgtc   7740
gcaaggacag agggctttct gtatcctggg ggcttgcctt ggtgtaccag aagaatcgaa   7800
tcccacctgg gcttggagaa tgagtgcaag gatttattga gtggatgtag ctctcagcag   7860
atggggaag ccagaagggg atggaatggg aagggtttcc cctggagtca gaccgctcag    7920
tggcccgggc tcggtggccc gggctcggtg gcctgggctc tcctccgact gcctcagcca   7980
aactccgcgt tgttctgctg gtcagtggcc tgccggtgcc tgttggtgag ttcttctcaa   8040
tgtccagctg tccttgcgtc cctccgctga tgtgctcctc ccgatgtcca gctacctgtg   8100
tgtctgcctg ctagggtctt ggggttttta taggcacatg atgggggcgt ggcaggccag   8160
ggtggttttg ggaaatgaaa catttaggca ggaaaacaaa aatgcctgtc ctcacctagg   8220
tccatgggca caggtctggg ggtggagccc tcgccaggga ccacaccctc ttctacccag   8280
cacttccctt ccctacttcc atatcattta aagggaccac gcccttccca gctcttccct   8340
tctgtatcac tgatgccttg ctctgtgttc tctaagtgga attatcactg tgtgtatgta   8400
caggtgtgtg catgtgtgtg catgtacctg tgcttttctt ttggaaaact agcacattac   8460
ctggattttg catctcaagg ataattctgt aagcaggaac ccttcctcct ttagaaggaa   8520
gtaaaggaga ggaaaatgct gtaaaactta catattaata attttttact ctatctcaaa   8580
cacgcatgcc tttaatcata gtcttaagag gaagatatct aattcataac ttactgtatg   8640
tagtcatcaa agaatatgag aaaaaattaa ctgaaaattt ttcttctggc tctaggaatt   8700
tgaagcctac attaatgctt ctggagaaca tggaattgtg gttttctctt tgggatcaat   8760
ggtctcagaa attccagaga agaaagctat ggcaattgct gatgctttgg gcaaaatccc   8820
tcagacagta agaagattct ataccatggc ctcatatcta ttttcacagg agcgctaatc   8880
ccagacttcc agcttccaga ttaattctct taattggaac cttagatttg cttttccct    8940
gccacttccc aactattaat ccaaaggttt ttttttgttgt tgtggttgtt gtcattgttt   9000
tcaatttgac tctcaaatac tctattaaac tatgatccac cacactcaga agtatcattt   9060
tctctaagag actcaaaagt gtattaggga gaatttattt aaaaataaaa taaatgggat   9120
attgtttctt catattaaat agaagtattt ctccaaaaag ctgttggtta gaacactgaa   9180
tttatgtctt acatttctgc tcttatagtt ctgcatccac ttgtttcatt aagcaaactt   9240
tcccttaaag tgcaggaaag tgaaaaaatc ctaagtgcac agcttgataa attatcacaa   9300
attcacgtag tgcatacacc cttgtaacta aacctccaaa acaagatgcc ggaagttgcc   9360
agtcctcaga agccttcaca gttactgatc ctcccactct gttaaagact gtgttccttc   9420
agaggacccc tgttttctag ttagtatagc agatttgttt tctaatcata ttatgttctt   9480
tctttacgtt ctgctctttt tgcccctccc aggtcctgtg gcggtacact ggaacccgac   9540
catcgaatct tgcgaacaac acgatacttg ttaagtggct accccaaaac gatctgcttg   9600
gtatgttggg cggattggat gtataggtca aaccagggtc aaattaagaa aatggcttaa   9660
gcacagctat tctaaaggat tgttgagctt gaaaatatta tggccaacat atcctacatt   9720
```

```
gctttttatc tagtggggta tctcaaccca cattttcttc tgcaaatttc tgcaagggca    9780
tgtgagtaac actgagtctt tggagtgttt tcagaaccta gatgtgtcca gctgtgaaac    9840
tcagagatgt aactgctgac atcctcccta ttttgcatct caggtcaccc gatgacccgt    9900
gcctttatca cccatgctgg ttcccatggt gtttatgaaa gcatatgcaa tggcgttccc    9960
atggtgatga tgcccttgtt tggtgatcag atggacaatg caaagcgcat ggagactaag   10020
ggagctggag tgaccctgaa tgttctgaaa tgacttctg aagatttaga aaatgctcta   10080
aaagcagtca tcaatgacaa aaggtaagaa agaagataca gaagaatact ttggtcatgg   10140
cattcatgat aaaattgttt caaatatgaa aacatttacg tagcatttaa tagcgttgtt   10200
tcaaatataa aaacaaatac ataaaaatct ggattttat ttcttctttt ttttttttt    10260
tttttttga gatggagtct tgctctgtca cctaggctgg agtgcagtgg tgcaatcttg   10320
gcttactgca acctccacct cccacgttca agcagttctg cctcagcctc cgtgtagctg   10380
ggattacagg tgtccaccac cacgcccggt aattttttgt attttttagt agagaaaggg   10440
tttcaccatg tttgtcaggc tggtcttgaa ctcctgactt caggtgatcc acctgcctcg   10500
gcctgccaaa gtgctgagat tacaggcatg agccagcgcg tctgacctgg atttataaat   10560
aagataattt agaggttatt attcactta taaaggatt ctttagtttc tatataatt    10620
atcatataat ttatttagaa ttttatttcc cccattagat ttaaaactcc aatttacata   10680
aaagttgcc ataatagaca tctgatccat aagtttcctg cacagaaaga aatactccat   10740
tataagaagc atagtatctt taagagaaaa acaactcaaa tgcttagaag tacagctttt   10800
tgcagcactg gaacctgtga gaaattttgt ccatggagtt tatgaatgaa ggagctataa   10860
gatatcacag acaaagtctt agaataagag caaggaaaa tttgctcaaa tgtggccctg   10920
aaaacgattc aaagggcaaa tgatttctgg attaaagtta gtatattact gtcaagctca   10980
ctggtaatag gcttattaga acctatggg aagaagtggt ggccagtggt agatttcatc   11040
cgacaataga tactgtgtgc atatgtgcgt gtgcgtttgt gcatgtggct gtgctcatgt   11100
gtgggtgcac acgtgtgcat tcatatgcgt gtgtgtgtgt gtgcgtgtgt ttatgagagt   11160
gtccattgct ttctcccatg gttacctcct ttagaaagaa gcagcagtca ggaagacaga   11220
tgtgaagagc tggagcatgt tcagatgaga ggagacggaa cacggggaca caccagcttg   11280
agcaagggac aacaggggag gactgatgac tgacttccca cctttgaggt gctaatgtgt   11340
gtgtggtggc actggataaa agatcaatgt tggctaggca ccatggcaca cgcctgtagt   11400
cccagccact ctggaggcta aggcgggagg attgcttgag cccagaagtt ggaggctgct   11460
atgagccgtg atcatgccac tgcactccag caacctgggc aacagagtga gaccctgtct   11520
caaaaaaaaa aaaaaaatg aaaagtccac ataacctgag catcatgtgc ccagagcgtt   11580
gggtggtgtg gtcccattcc ttccttccag cggcttcttc tggccacctc aatgtcagga   11640
tgtcctgctc acatatcaat accattaaaa cctgacttct ttccctgcac tgttgaagct   11700
ccttcttgag gctcacatta tggatataat tttgattctt tcttcagtgg tatagataac   11760
tacttgtaac ctaagaacaa cttggtgaaa gtcctctaat acattatttt ttaaaaaaac   11820
acaaatcaat gagctcaact tattaactaa ctttcatcta ttcatttttg agccatccct   11880
gtctgattgt gaatctccat gattccaaca ctctgagctg gggatagtgc ctacacaaaa   11940
taaaagaag tggaaaattt tcaaacatca gtttatgctg acaaccaggc cataataggt   12000
gctcaattac tattgaatga atgaatgaaa gttctggcca ggtacggtgg ctcatgcctg   12060
tagtcccaac actttgggag gccgaggcag gtggatcact tgaggttagg agttcgaaac   12120
```

```
caacctgacc aacatgaaga aaccttatct ctaccaaaaa aatataaaaa aattacccag   12180
gcatggtggt gtatgcctgt aatcccagct atttgggagg ctgaggcagg aaaatcactt   12240
gaacctgaga ggcggaggtt gcagtgagct gagattgtgc cactccactc cagcctgggc   12300
gacagagtga gactccgtct tactaaaaa aaaaaaaag aaggttccaa gaaaattcat    12360
cttaaggttt atgtaaaagg aagatgatat ttaacatgat tcatggccaa gtactaatat   12420
tacattataa taatgtttcc aaataacatt atagatatgt ttaaagacag tgtattaggc   12480
tgttcttgca ttgctgtaaa gaaataccca agactgggta atttataaag aaaagaggtt   12540
tcattggctc gtgtttctgc aggctgtaca ggaagcttag tgctgacatc acttggctgc   12600
cgggggaacc tcagggagct tttactcatg gcagaaggca atgcgggagc ttgcatgtca   12660
catggcaaaa gcaggagcga gagagagttg gggggaagg tgccacacac tttttaatga    12720
ccggctctca caataactca tgaaaactca ctatcaggaa gacagcacta aagcacaagg   12780
gatccgaccc catgatccaa acacctccca ccaggcccca tctccagcac tggggattac   12840
aattcaacat gagatctgag tgtggacaaa tatccaaact gtatcagtca acagcgatca   12900
taattagtcc tgaataggag tgcctttttt tttctttctt ctccctttc ttttctactt    12960 cctcctcctt ttccctctcc tcttcaatct cctcttcatt cctgtagcac caagggttga   13020
agcacctaac ccgttttgga ttgagatgtt ctgattgggc aatgaacact gtccagaata   13080
aacagaaatc cattttgcac taagtggctg cacagaccct gcctcatgct aaatctagca   13140
cccagatagt ttaatgtttc aatgactgaa ttacaaatat atcatcacct tggatttggc   13200
acttacaaat ggctgttaat ttggccagag gtggttgttt acaacttcaa ataggagact   13260
attcataatt tctgacgtga catttttcctt tctttatttt actgtatgaa aatataatga   13320
aatttctcac aaaatatcac taaaaagaaa agaagaagag taggaagcaa ggttaaaata   13380
tttctaaaat ataattttgg tctttctttt tctcccttcc ttcctccgtc cctctctcct   13440
ttcctctctc cctccctccc tccctccctt cctccttttcc ttgcttcctt ccctccttct   13500
cttccttctt tttcaagaga tcaataacat ttattaagaa taagtttctt aattataacc   13560
tttcaggtga taatagtaac acagcctggg caacacaata agaccttgtt tctacaaaaa   13620
atttaaaaat tggccagaca tagtggtgca tgactaattc cagctactct ggaggctgag   13680
gcaggaggat ggcttgagcc caggagttgg aggctgcagt tagccatgct tgtgccacta   13740
cactccagcc cgggcaacag ggcaagactc tgtatctaaa acaacaaca acaacaataa    13800 tagaaacagg tttcctttcc caagtttgga aaatctggta gtcttcttaa gcagccatga   13860
gcataaagag aggattgttc ataccacagg tgttccaggc ataacgaaac tgtctttgtg   13920
tttagttaca aggagaacat catgcgcctc tccagccttc acaaggaccg cccggtggag   13980
ccgctggacc tggccgtgtt ctgggtggag tttgtgatga ggcacaaggg cgcgccacac   14040
ctgcgccccg cagcccacga cctcacctgg taccagtacc attccttgga cgtgattggt   14100
ttcctcttgg ccgtcgtgct gacagtggcc ttcatcacct taaatgttg tgcttatggc   14160 taccggaaat gcttggggaa aaagggcga gttaagaaag cccacaaatc caagacccat   14220
tgagaagtgg gtgggaaata aggtaaaatt ttgaaccatt ccctagtcat ttccaaactt   14280
gaaaacagaa tcagtgttaa attcatttta ttcttattaa ggaaatactt tgcataaatt   14340
aatcagcccc agagtgcttt aaaaaattct cttaaataaa aataataagac tcgctagtca   14400 gtaaagatat ttgaatatgt atcgtgcccc ctccggtgtc tttgatcagg atgacatgtg   14460 ccattttca gaggacgtgc agacaggctg gcattctaga ttacttttct tactctgaaa   14520
```

```
catggcctgt tgggagtgc gggattcaaa ggtggtccca ccgctgcccc tactgcaaat    14580
ggcagtttta atcttatctt ttggcttctg cagatggttg caattgatcc ttaaccaata    14640
atggtcagtc ctcatctctg tcctgcttca taggtgccac cttgtgtgtt taaagaaggg    14700
aagctttgta cctttagagt gtaggtgaaa tgaatgaatg gcttggagtg cactgagaac    14760
agcatatgat ttcttgcttt ggggaaaaag aatgatgcta tgaaattggt gggtggtgta    14820
tttgagaaga taatcattgc ttatgtcaaa tggagctgaa tttgataaaa acccaaaata    14880
cagctatgaa gtgctgggca agtttacttt ttttctgatg tttcctacaa ctaaaaataa    14940
attaataaat ttatataaat tctatttaag tgttttcact ggtgtcgcat ttatttcttg    15000
ttaagttgca ttttctaatt acaaaagtaa tgcatgatta tgacagaaag tttggaaaat    15060
atagaggttc acacacacac gccttcattg cgtgtgcatg cataaatgca tgagaaaaga    15120
aaaataacca gtaatcgcat cgcccagaaa taaccccagt tacaattgtg gcaaatacac    15180
atacttataa atattgcaga tatattaagt atacctagta tttgctaaca ctctttcttc    15240
tactctgtca tgaagattct cccaaggtgt ttttgtataa tatttaattc attttcagtg    15300
gccaagcagt attctacttc atggatatac caggatttat ttaaccataa cttctggttg    15360
gattcactct tattattttg tttaattaaa aaaaaaagac ctcggctggg cacagtggct    15420
catgcctgta atcccagcac tttgggaggc cgaggtgggt ggatcaccta agatcgggag    15480
tttgagacca gcctggccaa catggcaaaa ccccgtctct actaaaaata cagaaaatta    15540
gccgggtgtg gttgccagca cctgtaattc cagctaattg ggaggctgag caggagaat    15600 tgcttgaacc ggggtcaggg ggttcggagg tcggaggttg cagtgagtcc ggatcatgcc    15660
actgcattcc agcctgggtg acacagccag actctgtctc aaaaacaaca acaacaacaa    15720
aacaacaaca acaacaacaa caaaaatctc actggacatc ctagtagcta aggctttcca    15780
catattcatg attacttctg ttggaaagtg ctttacaaca aattgctagt tgtctcagtc    15840
tgggttcccc tgagatgagg attcaagggc caggagttta tttaggaagt aaaggaaaca    15900
ctgatagagg agtggcagag tgagaagggg tgatggtcat ccacagctgg ctctcttgtg    15960
gtcaatcgga gcttaatcct gctgggtgac tctgggagcc agtggagaaa agacacccca    16020
gacttatccc aatgaggaac acggctgttg ggtgcttgag tacttgcctc gtcagggatt    16080
gaaacgtact cccaggtagt agtaatttct ctgcccttcc attaggccac aaaggggggct    16140 ctgacagaga gagctgacga gaaaaaacac acgcccttgt cactgaagag gtacacaggg    16200
gatctgtgtg gggcaccacc tgcactgcta ccctggacaa atagcttaag aaatccccac    16260
actgcatccc caaacttact atcagcgtgt gagggagaca ggttcccaca ccctcattag    16320
cacaaagtac tatcttgaaa agaaagcct gtcagtttga taggagaaaa gcaggatctt    16380
gtttacaatg tgcttttatt attgttatta ttagagattg tatttctttt caagctgatg    16440
agccgtctgt gtttatttt tggaggatac cctttgccca ctttcctatt ggagtgtatt    16500
accctgagga tttggtaaga gtgcttattg cattcaccag aatgtccttt ttgtcattta    16560
ctgtattttc tctactttt tttttttgcc ttgttttact tttttgttt tgtattacaa    16620 gcagaagttt taaatttgta agcttcaaat tggagctggg gtggtgcaga gcgaagattt    16680
cagctggttc cctgaccca gctccatctc cttccctagg cagtggctgg aacacattct    16740
gtccactatt tccctctcta catccttgag gctgtgcagt caccccctcaa ctacgttcac    16800 cctccttcaa agcccttcct ggtccacccg gggaccatct cccggcctca ctgcccctag    16860
```

-continued ctccttgacg ccccaacctc tctcagggac cccaagttgc catgacctcc agccagctca    16920
tgttcatttg caccttcgtg tctg                                           16944

<210> SEQ ID NO 2
<211> LENGTH: 22
<212> TYPE: DNA
<213> ORGANISM: Artificial
<220> FEATURE:
<223> OTHER INFORMATION: forward primer

<400> SEQUENCE: 2
gcagcagagg ggacatgaaa ta                                             22

<210> SEQ ID NO 3
<211> LENGTH: 21
<212> TYPE: DNA
<213> ORGANISM: Artificial
<220> FEATURE:
<223> OTHER INFORMATION: forward primer

<400> SEQUENCE: 3
cagcagaggg gacatgaaat a                                              21

<210> SEQ ID NO 4
<211> LENGTH: 20
<212> TYPE: DNA
<213> ORGANISM: Artificial
<220> FEATURE:
<223> OTHER INFORMATION: forward primer

<400> SEQUENCE: 4
agcagagggg acatgaaata                                                20

<210> SEQ ID NO 5
<211> LENGTH: 19
<212> TYPE: DNA
<213> ORGANISM: Artificial
<220> FEATURE:
<223> OTHER INFORMATION: forward primer

<400> SEQUENCE: 5
gcagagggga catgaaata                                                 19

<210> SEQ ID NO 6
<211> LENGTH: 18
<212> TYPE: DNA
<213> ORGANISM: Artificial
<220> FEATURE:
<223> OTHER INFORMATION: forward primer

<400> SEQUENCE: 6
cagaggggac atgaaata                                                  18

<210> SEQ ID NO 7
<211> LENGTH: 27
<212> TYPE: DNA
<213> ORGANISM: Artificial
<220> FEATURE:
<223> OTHER INFORMATION: reverse primer

<400> SEQUENCE: 7
ctcaaaaaca ttatgcccga gactaac                                        27

```
<210> SEQ ID NO 8
<211> LENGTH: 26
<212> TYPE: DNA
<213> ORGANISM: Artificial
<220> FEATURE:
<223> OTHER INFORMATION: reverse primer

<400> SEQUENCE: 8
tcaaaaacat tatgcccgag actaac                                          26

<210> SEQ ID NO 9
<211> LENGTH: 25
<212> TYPE: DNA
<213> ORGANISM: Artificial
<220> FEATURE:
<223> OTHER INFORMATION: reverse primer

<400> SEQUENCE: 9
caaaaacatt atgcccgaga ctaac                                           25

<210> SEQ ID NO 10
<211> LENGTH: 24
<212> TYPE: DNA
<213> ORGANISM: Artificial
<220> FEATURE:
<223> OTHER INFORMATION: reverse primer

<400> SEQUENCE: 10
aaaaacatta tgcccgagac taac                                            24

<210> SEQ ID NO 11
<211> LENGTH: 23
<212> TYPE: DNA
<213> ORGANISM: Artificial
<220> FEATURE:
<223> OTHER INFORMATION: reverse primer

<400> SEQUENCE: 11
aaaacattat gcccgagact aac                                             23

<210> SEQ ID NO 12
<211> LENGTH: 22
<212> TYPE: DNA
<213> ORGANISM: Artificial
<220> FEATURE:
<223> OTHER INFORMATION: reverse primer

<400> SEQUENCE: 12
aaacattatg cccgagacta ac                                              22

<210> SEQ ID NO 13
<211> LENGTH: 21
<212> TYPE: DNA
<213> ORGANISM: Artificial
<220> FEATURE:
<223> OTHER INFORMATION: reverse primer

<400> SEQUENCE: 13
aacattatgc ccgagactaa c                                               21

<210> SEQ ID NO 14
<211> LENGTH: 20
<212> TYPE: DNA
<213> ORGANISM: Artificial
<220> FEATURE:
<223> OTHER INFORMATION: reverse primer
```

```
<400> SEQUENCE: 14
acattatgcc cgagactaac                                              20

<210> SEQ ID NO 15
<211> LENGTH: 19
<212> TYPE: DNA
<213> ORGANISM: Artificial
<220> FEATURE:
<223> OTHER INFORMATION: reverse primer

<400> SEQUENCE: 15
cattatgccc gagactaac                                               19

<210> SEQ ID NO 16
<211> LENGTH: 18
<212> TYPE: DNA
<213> ORGANISM: Artificial
<220> FEATURE:
<223> OTHER INFORMATION: reverse primer

<400> SEQUENCE: 16
attatgcccg agactaac                                                18

<210> SEQ ID NO 17
<211> LENGTH: 17
<212> TYPE: DNA
<213> ORGANISM: Artificial
<220> FEATURE:
<223> OTHER INFORMATION: reverse primer

<400> SEQUENCE: 17
ttatgcccga gactaac                                                 17

<210> SEQ ID NO 18
<211> LENGTH: 21
<212> TYPE: DNA
<213> ORGANISM: Artificial
<220> FEATURE:
<223> OTHER INFORMATION: forward primer

<400> SEQUENCE: 18
cacagaactt tctgtgcgac g                                            21

<210> SEQ ID NO 19
<211> LENGTH: 20
<212> TYPE: DNA
<213> ORGANISM: Artificial
<220> FEATURE:
<223> OTHER INFORMATION: forward primer

<400> SEQUENCE: 19
acagaacttt ctgtgcgacg                                              20

<210> SEQ ID NO 20
<211> LENGTH: 19
<212> TYPE: DNA
<213> ORGANISM: Artificial
<220> FEATURE:
<223> OTHER INFORMATION: forward primer

<400> SEQUENCE: 20
cagaactttc tgtgcgacg                                               19
```

```
<210> SEQ ID NO 21
<211> LENGTH: 18
<212> TYPE: DNA
<213> ORGANISM: Artificial
<220> FEATURE:
<223> OTHER INFORMATION: forward primer

<400> SEQUENCE: 21
agaactttct gtgcgacg                                                    18

<210> SEQ ID NO 22
<211> LENGTH: 17
<212> TYPE: DNA
<213> ORGANISM: Artificial
<220> FEATURE:
<223> OTHER INFORMATION: forward primer

<400> SEQUENCE: 22
gaactttctg tgcgacg                                                     17

<210> SEQ ID NO 23
<211> LENGTH: 16
<212> TYPE: DNA
<213> ORGANISM: Artificial
<220> FEATURE:
<223> OTHER INFORMATION: forward primer

<400> SEQUENCE: 23
aactttctgt gcgacg                                                      16

<210> SEQ ID NO 24
<211> LENGTH: 15
<212> TYPE: DNA
<213> ORGANISM: Artificial
<220> FEATURE:
<223> OTHER INFORMATION: forward primer

<400> SEQUENCE: 24
actttctgtg cgacg                                                       15

<210> SEQ ID NO 25
<211> LENGTH: 24
<212> TYPE: DNA
<213> ORGANISM: Artificial
<220> FEATURE:
<223> OTHER INFORMATION: reverse primer

<400> SEQUENCE: 25
cagacagatg cagagctcaa tagg                                             24

<210> SEQ ID NO 26
<211> LENGTH: 23
<212> TYPE: DNA
<213> ORGANISM: Artificial
<220> FEATURE:
<223> OTHER INFORMATION: reverse primer

<400> SEQUENCE: 26
agacagatgc agagctcaat agg                                              23

<210> SEQ ID NO 27
<211> LENGTH: 22
<212> TYPE: DNA
<213> ORGANISM: Artificial
<220> FEATURE:
<223> OTHER INFORMATION: reverse primer
```

```
<400> SEQUENCE: 27
gacagatgca gagctcaata gg                                              22

<210> SEQ ID NO 28
<211> LENGTH: 21
<212> TYPE: DNA
<213> ORGANISM: Artificial
<220> FEATURE:
<223> OTHER INFORMATION: reverse primer

<400> SEQUENCE: 28
acagatgcag agctcaatag g                                               21

<210> SEQ ID NO 29
<211> LENGTH: 20
<212> TYPE: DNA
<213> ORGANISM: Artificial
<220> FEATURE:
<223> OTHER INFORMATION: reverse primer

<400> SEQUENCE: 29
cagatgcaga gctcaatagg                                                 20

<210> SEQ ID NO 30
<211> LENGTH: 19
<212> TYPE: DNA
<213> ORGANISM: Artificial
<220> FEATURE:
<223> OTHER INFORMATION: reverse primer

<400> SEQUENCE: 30
agatgcagag ctcaatagg                                                  19

<210> SEQ ID NO 31
<211> LENGTH: 18
<212> TYPE: DNA
<213> ORGANISM: Artificial
<220> FEATURE:
<223> OTHER INFORMATION: reverse primer

<400> SEQUENCE: 31
gatgcagagc tcaatagg                                                   18

<210> SEQ ID NO 32
<211> LENGTH: 17
<212> TYPE: DNA
<213> ORGANISM: Artificial
<220> FEATURE:
<223> OTHER INFORMATION: reverse primer

<400> SEQUENCE: 32
atgcagagct caatagg                                                    17

<210> SEQ ID NO 33
<211> LENGTH: 29
<212> TYPE: DNA
<213> ORGANISM: Artificial
<220> FEATURE:
<223> OTHER INFORMATION: forward primer

<400> SEQUENCE: 33
ctttttatag tcacgtgaca cagtcaaac                                       29
```

```
<210> SEQ ID NO 34
<211> LENGTH: 28
<212> TYPE: DNA
<213> ORGANISM: Artificial
<220> FEATURE:
<223> OTHER INFORMATION: forward primer

<400> SEQUENCE: 34
tttttatagt cacgtgacac agtcaaac                                    28

<210> SEQ ID NO 35
<211> LENGTH: 27
<212> TYPE: DNA
<213> ORGANISM: Artificial
<220> FEATURE:
<223> OTHER INFORMATION: forward primer

<400> SEQUENCE: 35
ttttatagtc acgtgacaca gtcaaac                                     27

<210> SEQ ID NO 36
<211> LENGTH: 26
<212> TYPE: DNA
<213> ORGANISM: Artificial
<220> FEATURE:
<223> OTHER INFORMATION: forward primer

<400> SEQUENCE: 36
tttatagtca cgtgacacag tcaaac                                      26

<210> SEQ ID NO 37
<211> LENGTH: 25
<212> TYPE: DNA
<213> ORGANISM: Artificial
<220> FEATURE:
<223> OTHER INFORMATION: forward primer

<400> SEQUENCE: 37
ttatagtcac gtgacacagt caaac                                       25

<210> SEQ ID NO 38
<211> LENGTH: 24
<212> TYPE: DNA
<213> ORGANISM: Artificial
<220> FEATURE:
<223> OTHER INFORMATION: forward primer

<400> SEQUENCE: 38
tatagtcacg tgacacagtc aaac                                        24

<210> SEQ ID NO 39
<211> LENGTH: 23
<212> TYPE: DNA
<213> ORGANISM: Artificial
<220> FEATURE:
<223> OTHER INFORMATION: forward primer

<400> SEQUENCE: 39
atagtcacgt gacacagtca aac                                         23

<210> SEQ ID NO 40
<211> LENGTH: 22
<212> TYPE: DNA
<213> ORGANISM: Artificial
<220> FEATURE:
<223> OTHER INFORMATION: forward primer
```

```
<400> SEQUENCE: 40
tagtcacgtg acacagtcaa ac                                              22

<210> SEQ ID NO 41
<211> LENGTH: 21
<212> TYPE: DNA
<213> ORGANISM: Artificial
<220> FEATURE:
<223> OTHER INFORMATION: forward primer

<400> SEQUENCE: 41
agtcacgtga cacagtcaaa c                                               21

<210> SEQ ID NO 42
<211> LENGTH: 20
<212> TYPE: DNA
<213> ORGANISM: Artificial
<220> FEATURE:
<223> OTHER INFORMATION: forward primer

<400> SEQUENCE: 42
gtcacgtgac acagtcaaac                                                 20

<210> SEQ ID NO 43
<211> LENGTH: 19
<212> TYPE: DNA
<213> ORGANISM: Artificial
<220> FEATURE:
<223> OTHER INFORMATION: forward primer

<400> SEQUENCE: 43
tcacgtgaca cagtcaaac                                                  19

<210> SEQ ID NO 44
<211> LENGTH: 18
<212> TYPE: DNA
<213> ORGANISM: Artificial
<220> FEATURE:
<223> OTHER INFORMATION: forward primer

<400> SEQUENCE: 44
cacgtgacac agtcaaac                                                   18

<210> SEQ ID NO 45
<211> LENGTH: 17
<212> TYPE: DNA
<213> ORGANISM: Artificial
<220> FEATURE:
<223> OTHER INFORMATION: forward primer

<400> SEQUENCE: 45
acgtgacaca gtcaaac                                                    17

<210> SEQ ID NO 46
<211> LENGTH: 20
<212> TYPE: DNA
<213> ORGANISM: Artificial
<220> FEATURE:
<223> OTHER INFORMATION: reverse primer

<400> SEQUENCE: 46
cgcctttgct cctgccagag                                                 20
```

```
<210> SEQ ID NO 47
<211> LENGTH: 19
<212> TYPE: DNA
<213> ORGANISM: Artificial
<220> FEATURE:
<223> OTHER INFORMATION: reverse primer

<400> SEQUENCE: 47
gcctttgctc ctgccagag                                            19

<210> SEQ ID NO 48
<211> LENGTH: 18
<212> TYPE: DNA
<213> ORGANISM: Artificial
<220> FEATURE:
<223> OTHER INFORMATION: reverse primer

<400> SEQUENCE: 48
cctttgctcc tgccagag                                             18

<210> SEQ ID NO 49
<211> LENGTH: 17
<212> TYPE: DNA
<213> ORGANISM: Artificial
<220> FEATURE:
<223> OTHER INFORMATION: reverse primer

<400> SEQUENCE: 49
ctttgctcct gccagag                                              17

<210> SEQ ID NO 50
<211> LENGTH: 16
<212> TYPE: DNA
<213> ORGANISM: Artificial
<220> FEATURE:
<223> OTHER INFORMATION: reverse primer

<400> SEQUENCE: 50
tttgctcctg ccagag                                               16

<210> SEQ ID NO 51
<211> LENGTH: 24
<212> TYPE: DNA
<213> ORGANISM: Artificial
<220> FEATURE:
<223> OTHER INFORMATION: probe

<400> SEQUENCE: 51
catcagagac agagcatttt acac                                      24

<210> SEQ ID NO 52
<211> LENGTH: 23
<212> TYPE: DNA
<213> ORGANISM: Artificial
<220> FEATURE:
<223> OTHER INFORMATION: probe

<400> SEQUENCE: 52
atcagagaca gagcatttta cac                                       23

<210> SEQ ID NO 53
<211> LENGTH: 22
<212> TYPE: DNA
<213> ORGANISM: Artificial
<220> FEATURE:
<223> OTHER INFORMATION: probe
```

```
<400> SEQUENCE: 53
tcagagacag agcattttac ac                                          22

<210> SEQ ID NO 54
<211> LENGTH: 21
<212> TYPE: DNA
<213> ORGANISM: Artificial
<220> FEATURE:
<223> OTHER INFORMATION: probe

<400> SEQUENCE: 54
cagagacaga gcattttaca c                                           21

<210> SEQ ID NO 55
<211> LENGTH: 20
<212> TYPE: DNA
<213> ORGANISM: Artificial
<220> FEATURE:
<223> OTHER INFORMATION: probe

<400> SEQUENCE: 55
agagacagag cattttacac                                             20

<210> SEQ ID NO 56
<211> LENGTH: 19
<212> TYPE: DNA
<213> ORGANISM: Artificial
<220> FEATURE:
<223> OTHER INFORMATION: probe

<400> SEQUENCE: 56
gagacagagc attttacac                                              19

<210> SEQ ID NO 57
<211> LENGTH: 18
<212> TYPE: DNA
<213> ORGANISM: Artificial
<220> FEATURE:
<223> OTHER INFORMATION: probe

<400> SEQUENCE: 57
agacagagca ttttacac                                               18

<210> SEQ ID NO 58
<211> LENGTH: 17
<212> TYPE: DNA
<213> ORGANISM: Artificial
<220> FEATURE:
<223> OTHER INFORMATION: probe

<400> SEQUENCE: 58
gacagagcat tttacac                                                17

<210> SEQ ID NO 59
<211> LENGTH: 23
<212> TYPE: DNA
<213> ORGANISM: Artificial
<220> FEATURE:
<223> OTHER INFORMATION: probe

<400> SEQUENCE: 59
tggtttattc ccagtatgca acc                                         23
```

```
<210> SEQ ID NO 60
<211> LENGTH: 22
<212> TYPE: DNA
<213> ORGANISM: Artificial
<220> FEATURE:
<223> OTHER INFORMATION: probe

<400> SEQUENCE: 60
ggtttattcc cagtatgcaa cc                                              22

<210> SEQ ID NO 61
<211> LENGTH: 20
<212> TYPE: DNA
<213> ORGANISM: Artificial
<220> FEATURE:
<223> OTHER INFORMATION: probe

<400> SEQUENCE: 61
tttattccca gtatgcaacc                                                 20

<210> SEQ ID NO 62
<211> LENGTH: 19
<212> TYPE: DNA
<213> ORGANISM: Artificial
<220> FEATURE:
<223> OTHER INFORMATION: probe

<400> SEQUENCE: 62
ttattcccag tatgcaacc                                                  19

<210> SEQ ID NO 63
<211> LENGTH: 18
<212> TYPE: DNA
<213> ORGANISM: Artificial
<220> FEATURE:
<223> OTHER INFORMATION: probe

<400> SEQUENCE: 63
tattcccagt atgcaacc                                                   18

<210> SEQ ID NO 64
<211> LENGTH: 17
<212> TYPE: DNA
<213> ORGANISM: Artificial
<220> FEATURE:
<223> OTHER INFORMATION: probe

<400> SEQUENCE: 64
attcccagta tgcaacc                                                    17

<210> SEQ ID NO 65
<211> LENGTH: 16
<212> TYPE: DNA
<213> ORGANISM: Artificial
<220> FEATURE:
<223> OTHER INFORMATION: probe

<400> SEQUENCE: 65
ttcccagtat gcaacc                                                     16

<210> SEQ ID NO 66
<211> LENGTH: 15
<212> TYPE: DNA
<213> ORGANISM: Artificial
<220> FEATURE:
<223> OTHER INFORMATION: probe
```

```
<400> SEQUENCE: 66
tcccagtatg caacc                                               15

<210> SEQ ID NO 67
<211> LENGTH: 31
<212> TYPE: DNA
<213> ORGANISM: Artificial
<220> FEATURE:
<223> OTHER INFORMATION: probe

<400> SEQUENCE: 67
ccatatatat atatatataa gtaggagagg g                             31

<210> SEQ ID NO 68
<211> LENGTH: 30
<212> TYPE: DNA
<213> ORGANISM: Artificial
<220> FEATURE:
<223> OTHER INFORMATION: probe

<400> SEQUENCE: 68
ccatatatat atatatataa gtaggagagg                               30

<210> SEQ ID NO 69
<211> LENGTH: 29
<212> TYPE: DNA
<213> ORGANISM: Artificial
<220> FEATURE:
<223> OTHER INFORMATION: probe

<400> SEQUENCE: 69
ccatatatat atatatataa gtaggagag                                29

<210> SEQ ID NO 70
<211> LENGTH: 28
<212> TYPE: DNA
<213> ORGANISM: Artificial
<220> FEATURE:
<223> OTHER INFORMATION: probe

<400> SEQUENCE: 70
ccatatatat atatatataa gtaggaga                                 28

<210> SEQ ID NO 71
<211> LENGTH: 27
<212> TYPE: DNA
<213> ORGANISM: Artificial
<220> FEATURE:
<223> OTHER INFORMATION: probe

<400> SEQUENCE: 71
ccatatatat atatatataa gtaggag                                  27

<210> SEQ ID NO 72
<211> LENGTH: 26
<212> TYPE: DNA
<213> ORGANISM: Artificial
<220> FEATURE:
<223> OTHER INFORMATION: probe

<400> SEQUENCE: 72
ccatatatat atatatataa gtagga                                   26
```

```
<210> SEQ ID NO 73
<211> LENGTH: 25
<212> TYPE: DNA
<213> ORGANISM: Artificial
<220> FEATURE:
<223> OTHER INFORMATION: probe

<400> SEQUENCE: 73
ccatatatat atatatataa gtagg                                           25

<210> SEQ ID NO 74
<211> LENGTH: 34
<212> TYPE: DNA
<213> ORGANISM: Artificial
<220> FEATURE:
<223> OTHER INFORMATION: forward primer

<400> SEQUENCE: 74
ggggacatga aatagttgtc ctagcacctg acgc                                 34

<210> SEQ ID NO 75
<211> LENGTH: 33
<212> TYPE: DNA
<213> ORGANISM: Artificial
<220> FEATURE:
<223> OTHER INFORMATION: forward primer

<400> SEQUENCE: 75
gggacatgaa atagttgtcc tagcacctga cgc                                  33

<210> SEQ ID NO 76
<211> LENGTH: 32
<212> TYPE: DNA
<213> ORGANISM: Artificial
<220> FEATURE:
<223> OTHER INFORMATION: forward primer

<400> SEQUENCE: 76
ggacatgaaa tagttgtcct agcacctgac gc                                   32

<210> SEQ ID NO 77
<211> LENGTH: 31
<212> TYPE: DNA
<213> ORGANISM: Artificial
<220> FEATURE:
<223> OTHER INFORMATION: forward primer

<400> SEQUENCE: 77
gacatgaaat agttgtccta gcacctgacg c                                    31

<210> SEQ ID NO 78
<211> LENGTH: 30
<212> TYPE: DNA
<213> ORGANISM: Artificial
<220> FEATURE:
<223> OTHER INFORMATION: forward primer

<400> SEQUENCE: 78
acatgaaata gttgtcctag cacctgacgc                                      30

<210> SEQ ID NO 79
<211> LENGTH: 29
<212> TYPE: DNA
<213> ORGANISM: Artificial
<220> FEATURE:
<223> OTHER INFORMATION: forward primer
```

```
<400> SEQUENCE: 79
catgaaatag ttgtcctagc acctgacgc                                    29

<210> SEQ ID NO 80
<211> LENGTH: 28
<212> TYPE: DNA
<213> ORGANISM: Artificial
<220> FEATURE:
<223> OTHER INFORMATION: forward primer

<400> SEQUENCE: 80
atgaaatagt tgtcctagca cctgacgc                                     28

<210> SEQ ID NO 81
<211> LENGTH: 27
<212> TYPE: DNA
<213> ORGANISM: Artificial
<220> FEATURE:
<223> OTHER INFORMATION: forward primer

<400> SEQUENCE: 81
tgaaatagtt gtcctagcac ctgacgc                                      27

<210> SEQ ID NO 82
<211> LENGTH: 26
<212> TYPE: DNA
<213> ORGANISM: Artificial
<220> FEATURE:
<223> OTHER INFORMATION: forward primer

<400> SEQUENCE: 82
gaaatagttg tcctagcacc tgacgc                                       26

<210> SEQ ID NO 83
<211> LENGTH: 25
<212> TYPE: DNA
<213> ORGANISM: Artificial
<220> FEATURE:
<223> OTHER INFORMATION: forward primer

<400> SEQUENCE: 83
aaatagttgt cctagcacct gacgc                                        25

<210> SEQ ID NO 84
<211> LENGTH: 24
<212> TYPE: DNA
<213> ORGANISM: Artificial
<220> FEATURE:
<223> OTHER INFORMATION: forward primer

<400> SEQUENCE: 84
aatagttgtc ctagcacctg acgc                                         24

<210> SEQ ID NO 85
<211> LENGTH: 23
<212> TYPE: DNA
<213> ORGANISM: Artificial
<220> FEATURE:
<223> OTHER INFORMATION: forward primer

<400> SEQUENCE: 85
atagttgtcc tagcacctga cgc                                          23
```

```
<210> SEQ ID NO 86
<211> LENGTH: 22
<212> TYPE: DNA
<213> ORGANISM: Artificial
<220> FEATURE:
<223> OTHER INFORMATION: forward primer

<400> SEQUENCE: 86
tagttgtcct agcacctgac gc                                              22

<210> SEQ ID NO 87
<211> LENGTH: 21
<212> TYPE: DNA
<213> ORGANISM: Artificial
<220> FEATURE:
<223> OTHER INFORMATION: forward primer

<400> SEQUENCE: 87
agttgtccta gcacctgacg c                                               21

<210> SEQ ID NO 88
<211> LENGTH: 20
<212> TYPE: DNA
<213> ORGANISM: Artificial
<220> FEATURE:
<223> OTHER INFORMATION: forward primer

<400> SEQUENCE: 88
gttgtcctag cacctgacgc                                                 20

<210> SEQ ID NO 89
<211> LENGTH: 19
<212> TYPE: DNA
<213> ORGANISM: Artificial
<220> FEATURE:
<223> OTHER INFORMATION: forward primer

<400> SEQUENCE: 89
ttgtcctagc acctgacgc                                                  19

<210> SEQ ID NO 90
<211> LENGTH: 18
<212> TYPE: DNA
<213> ORGANISM: Artificial
<220> FEATURE:
<223> OTHER INFORMATION: forward primer

<400> SEQUENCE: 90
tgtcctagca cctgacgc                                                   18

<210> SEQ ID NO 91
<211> LENGTH: 29
<212> TYPE: DNA
<213> ORGANISM: Artificial
<220> FEATURE:
<223> OTHER INFORMATION: reverse primer

<400> SEQUENCE: 91
caaaagactc tttcacatcc tccctttgg                                       29

<210> SEQ ID NO 92
<211> LENGTH: 27
<212> TYPE: DNA
<213> ORGANISM: Artificial
<220> FEATURE:
<223> OTHER INFORMATION: forward primer
```

```
<400> SEQUENCE: 92
ccttttcaca gaactttctg tgcgacg                                           27

<210> SEQ ID NO 93
<211> LENGTH: 26
<212> TYPE: DNA
<213> ORGANISM: Artificial
<220> FEATURE:
<223> OTHER INFORMATION: forward primer

<400> SEQUENCE: 93
cttttcacag aactttctgt gcgacg                                            26

<210> SEQ ID NO 94
<211> LENGTH: 25
<212> TYPE: DNA
<213> ORGANISM: Artificial
<220> FEATURE:
<223> OTHER INFORMATION: forward primer

<400> SEQUENCE: 94
ttttcacaga actttctgtg cgacg                                             25

<210> SEQ ID NO 95
<211> LENGTH: 24
<212> TYPE: DNA
<213> ORGANISM: Artificial
<220> FEATURE:
<223> OTHER INFORMATION: forward primer

<400> SEQUENCE: 95
tttcacagaa ctttctgtgc gacg                                              24

<210> SEQ ID NO 96
<211> LENGTH: 23
<212> TYPE: DNA
<213> ORGANISM: Artificial
<220> FEATURE:
<223> OTHER INFORMATION: forward primer

<400> SEQUENCE: 96
ttcacagaac ttctgtgcg acg                                                23

<210> SEQ ID NO 97
<211> LENGTH: 22
<212> TYPE: DNA
<213> ORGANISM: Artificial
<220> FEATURE:
<223> OTHER INFORMATION: forward primer

<400> SEQUENCE: 97
tcacagaact ttctgtgcga cg                                                22

<210> SEQ ID NO 98
<211> LENGTH: 26
<212> TYPE: DNA
<213> ORGANISM: Artificial
<220> FEATURE:
<223> OTHER INFORMATION: reverse primer

<400> SEQUENCE: 98
gccagacaga tgcagagctc aatagg                                            26
```

```
<210> SEQ ID NO 99
<211> LENGTH: 25
<212> TYPE: DNA
<213> ORGANISM: Artificial
<220> FEATURE:
<223> OTHER INFORMATION: reverse primer

<400> SEQUENCE: 99
ccagacagat gcagagctca atagg                                            25

<210> SEQ ID NO 100
<211> LENGTH: 22
<212> TYPE: DNA
<213> ORGANISM: Artificial
<220> FEATURE:
<223> OTHER INFORMATION: probe

<400> SEQUENCE: 100
gggttgcata ctgggaataa ac                                               22

<210> SEQ ID NO 101
<211> LENGTH: 20
<212> TYPE: DNA
<213> ORGANISM: Artificial
<220> FEATURE:
<223> OTHER INFORMATION: probe

<400> SEQUENCE: 101
ggttgcatac tgggaataaa                                                  20

<210> SEQ ID NO 102
<211> LENGTH: 20
<212> TYPE: DNA
<213> ORGANISM: Artificial
<220> FEATURE:
<223> OTHER INFORMATION: probe

<400> SEQUENCE: 102
gttgcatact gggaataaac                                                  20

<210> SEQ ID NO 103
<211> LENGTH: 19
<212> TYPE: DNA
<213> ORGANISM: Artificial
<220> FEATURE:
<223> OTHER INFORMATION: probe

<400> SEQUENCE: 103
ttgcatactg ggaataaac                                                   19

<210> SEQ ID NO 104
<211> LENGTH: 18
<212> TYPE: DNA
<213> ORGANISM: Artificial
<220> FEATURE:
<223> OTHER INFORMATION: probe

<400> SEQUENCE: 104
tgcatactgg gaataaac                                                    18

<210> SEQ ID NO 105
<211> LENGTH: 17
<212> TYPE: DNA
<213> ORGANISM: Artificial
<220> FEATURE:
<223> OTHER INFORMATION: probe
```

```
<400> SEQUENCE: 105
gcatactggg aataaac                                                     17

<210> SEQ ID NO 106
<211> LENGTH: 39
<212> TYPE: DNA
<213> ORGANISM: Artificial
<220> FEATURE:
<223> OTHER INFORMATION: primer

<400> SEQUENCE: 106
ccgagactaa caaaagactc tttcacatcc tccctttgg                             39

<210> SEQ ID NO 107
<211> LENGTH: 38
<212> TYPE: DNA
<213> ORGANISM: Artificial
<220> FEATURE:
<223> OTHER INFORMATION: primer

<400> SEQUENCE: 107
cgagactaac aaaagactct ttcacatcct ccctttgg                              38

<210> SEQ ID NO 108
<211> LENGTH: 37
<212> TYPE: DNA
<213> ORGANISM: Artificial
<220> FEATURE:
<223> OTHER INFORMATION: primer

<400> SEQUENCE: 108
gagactaaca aaagactctt tcacatcctc cctttgg                               37

<210> SEQ ID NO 109
<211> LENGTH: 36
<212> TYPE: DNA
<213> ORGANISM: Artificial
<220> FEATURE:
<223> OTHER INFORMATION: primer

<400> SEQUENCE: 109
agactaacaa aagactcttt cacatcctcc ctttgg                                36

<210> SEQ ID NO 110
<211> LENGTH: 35
<212> TYPE: DNA
<213> ORGANISM: Artificial
<220> FEATURE:
<223> OTHER INFORMATION: primer

<400> SEQUENCE: 110
gactaacaaa agactctttc acatcctccc tttgg                                 35

<210> SEQ ID NO 111
<211> LENGTH: 34
<212> TYPE: DNA
<213> ORGANISM: Artificial
<220> FEATURE:
<223> OTHER INFORMATION: primer

<400> SEQUENCE: 111
actaacaaaa gactctttca catcctccct ttgg                                  34
```

```
<210> SEQ ID NO 112
<211> LENGTH: 33
<212> TYPE: DNA
<213> ORGANISM: Artificial
<220> FEATURE:
<223> OTHER INFORMATION: primer

<400> SEQUENCE: 112
ctaacaaaag actctttcac atcctcccctt tgg                                    33

<210> SEQ ID NO 113
<211> LENGTH: 32
<212> TYPE: DNA
<213> ORGANISM: Artificial
<220> FEATURE:
<223> OTHER INFORMATION: primer

<400> SEQUENCE: 113
taacaaagaa ctctttcaca tcctccctttt gg                                     32

<210> SEQ ID NO 114
<211> LENGTH: 31
<212> TYPE: DNA
<213> ORGANISM: Artificial
<220> FEATURE:
<223> OTHER INFORMATION: primer

<400> SEQUENCE: 114
aacaaaagac tctttcacat cctcccttttg g                                      31

<210> SEQ ID NO 115
<211> LENGTH: 30
<212> TYPE: DNA
<213> ORGANISM: Artificial
<220> FEATURE:
<223> OTHER INFORMATION: primer

<400> SEQUENCE: 115
acaaaagact ctttcacatc ctcccttttgg                                        30

<210> SEQ ID NO 116
<211> LENGTH: 28
<212> TYPE: DNA
<213> ORGANISM: Artificial
<220> FEATURE:
<223> OTHER INFORMATION: primer

<400> SEQUENCE: 116
aaaagactct ttcacatcct cccttttgg                                          28

<210> SEQ ID NO 117
<211> LENGTH: 27
<212> TYPE: DNA
<213> ORGANISM: Artificial
<220> FEATURE:
<223> OTHER INFORMATION: primer

<400> SEQUENCE: 117
aaagactctt tcacatcctc cctttgg                                            27

<210> SEQ ID NO 118
<211> LENGTH: 26
<212> TYPE: DNA
<213> ORGANISM: Artificial
<220> FEATURE:
<223> OTHER INFORMATION: primer
```

```
<400> SEQUENCE: 118
aagactcttt cacatcctcc ctttgg                                          26

<210> SEQ ID NO 119
<211> LENGTH: 25
<212> TYPE: DNA
<213> ORGANISM: Artificial
<220> FEATURE:
<223> OTHER INFORMATION: primer

<400> SEQUENCE: 119
agactctttc acatcctccc tttgg                                           25

<210> SEQ ID NO 120
<211> LENGTH: 24
<212> TYPE: DNA
<213> ORGANISM: Artificial
<220> FEATURE:
<223> OTHER INFORMATION: primer

<400> SEQUENCE: 120
gactctttca catcctccct ttgg                                            24

<210> SEQ ID NO 121
<211> LENGTH: 23
<212> TYPE: DNA
<213> ORGANISM: Artificial
<220> FEATURE:
<223> OTHER INFORMATION: primer

<400> SEQUENCE: 121
actctttcac atcctccctt tgg                                             23

<210> SEQ ID NO 122
<211> LENGTH: 22
<212> TYPE: DNA
<213> ORGANISM: Artificial
<220> FEATURE:
<223> OTHER INFORMATION: primer

<400> SEQUENCE: 122
ctctttcaca tcctcccttt gg                                              22

<210> SEQ ID NO 123
<211> LENGTH: 31
<212> TYPE: DNA
<213> ORGANISM: Artificial
<220> FEATURE:
<223> OTHER INFORMATION: primer

<400> SEQUENCE: 123 agcttttat agtcacgtga cacagtcaaa c                                     31

<210> SEQ ID NO 124
<211> LENGTH: 30
<212> TYPE: DNA
<213> ORGANISM: Artificial
<220> FEATURE:
<223> OTHER INFORMATION: primer

<400> SEQUENCE: 124 gcttttata gtcacgtgac acagtcaaac                                       30
```